(12) United States Patent
Rommelspacher

(10) Patent No.: US 8,334,299 B2
(45) Date of Patent: Dec. 18, 2012

(54) β-CARBOLINE FOR THE TREATMENT OF NEURODEGENERATIVE DISEASES

(75) Inventor: Hans Rommelspacher, Berlin (DE)

(73) Assignee: Ellneuroxx, Ltd., Neuss (DE)

( * ) Notice: Subject to any disclaimer, the term of this patent is extended or adjusted under 35 U.S.C. 154(b) by 396 days.

(21) Appl. No.: 12/528,771

(22) PCT Filed: Feb. 26, 2008

(86) PCT No.: PCT/DE2008/000332
§ 371 (c)(1), (2), (4) Date: Jan. 5, 2010

(87) PCT Pub. No.: WO2008/104161
PCT Pub. Date: Sep. 4, 2008

(65) Prior Publication Data
US 2010/0143474 A1   Jun. 10, 2010

(30) Foreign Application Priority Data

Feb. 26, 2007   (DE) .......................... 10 2007 009 264

(51) Int. Cl.
*A61K 31/437*   (2006.01)
*C07D 471/04*   (2006.01)
(52) U.S. Cl. ......................................... 514/292; 546/85
(58) Field of Classification Search .................. 514/292; 546/85
See application file for complete search history.

(56) References Cited

U.S. PATENT DOCUMENTS

| | | | |
|---|---|---|---|
| 2,767,179 A | 10/1956 | Cavallito et al. | |
| 2,850,501 A | 9/1958 | Voegtli | |
| 3,663,559 A | 5/1972 | Derijckere et al. | |
| 4,731,358 A | 3/1988 | Huth et al. | |
| 5,604,236 A | 2/1997 | Jakubowski et al. | |
| 2004/0180904 A1* | 9/2004 | Beck ........................ | 514/254.06 |
| 2009/0227619 A1 | 9/2009 | Wu et al. | |

FOREIGN PATENT DOCUMENTS

| | | |
|---|---|---|
| DE | 1044821 | 11/1958 |
| DE | 4223164 | 1/1993 |
| GB | 2155462 | 9/1985 |

OTHER PUBLICATIONS

Balon et al. Photochemistry and Photobiology 1998, 67, 414-419.*
WebMD Prevention of Parkinson's Disease, http://www.webmd.com/parkinsons-disease/guide/parkinsons-disease-prevention, obtained Mar. 2, 2012.*
Hamann et al. Neurochemistry International 2008, 52, 688-700, which was available online Sep. 4, 2007.*
Polanski et al. Journal of Neurochemistry, 2010, 113, 1659-1675.*
Cao et al., European Journal of Medicinal Chemistry, vol. 40, No. 10, Oct. 1, 2005, pp. 991-1001.
Bracher F et al., Pharmazie, vol. 50, No. 3, Mar. 1, 1995, p. 182/183, Figures.
Balon M et al., Photochemistry and Photobiology, vol. 67, No. 4, Apr. 1, 1998, pp. 414-419.
Matsubara, Kazuo et al., Journal of Neurochemistry (1998), 70(2), 727-735.
Won Tae Choi et al., Neurochemical Research, vol. 29, No. 10, Oct. 1, 2004, pp. 1807-1816.
Written Opinion for PCT/DE2008/000332 issued Jul. 21, 2008.
International Report on Patentability for PCT/DE2008/000332 issued Oct. 13, 2009.
Gruss et al. "9-methyl-β-carboline-induced cognitive enhancement is associated with elevated hippocampal dopamine levels and dendritic and synaptic proliferation" Journal of Neurology, Unpublished Article, Accepted Jan. 31, 2012.
Bekinschtein et al. "BDNF is essential to promote persistence of long-term memory storage" PNAS, 2008, vol. 105(7), 2711-2716.

* cited by examiner

*Primary Examiner* — Joseph Kosack
*Assistant Examiner* — Matthew Coughlin
(74) *Attorney, Agent, or Firm* — Meyertons, Hood, Kivlin, Kowert & Goetzel, P.C.; Eric B. Meyertons

(57) ABSTRACT

The embodiments relate to derivatives of 9-alkyl-β-carboline, their production and pharmaceutical compositions containing these 9-alkyl-β-carboline derivatives. Further, the use of 9-alkyl-β-carboline derivatives and pharmaceutical compositions for the treatment and prevention of movement disorders, neurodegenerative diseases, Alzheimer's disease and Parkinson's disease is described. Additionally, these effects can be utilized for the cultivation of cells such as dopaminergic cells or stem cells which shall be engrafted for the treatment of Parkinson's disease.

3 Claims, 8 Drawing Sheets

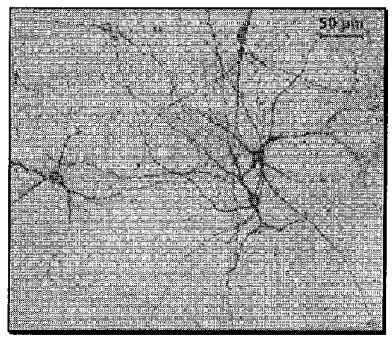 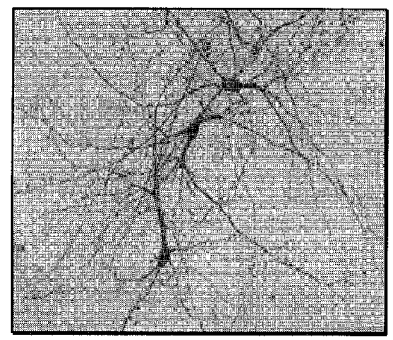
FIG. 1A          FIG. 1B
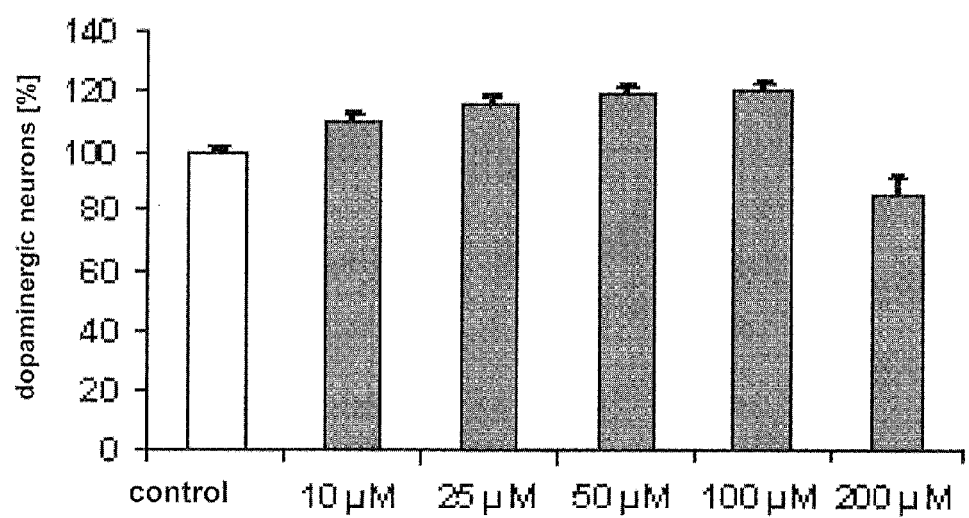
FIG. 1C

β-CARBOLINE FOR THE TREATMENT OF NEURODEGENERATIVE DISEASES

BACKGROUND OF THE INVENTION

1. Field of the Invention

The invention relates to derivatives of β-carbolines, preferably 9-alkyl-β-carbolines (9-alkyl-BC), the production thereof and their use for prophylaxis and treatment of neurodegenerative diseases and pharmaceutical compositions containing these derivatives.

2. Description of the Relevant Art

The compounds according to the invention shall be used in particular in Parkinson's disease. Parkinson's disease, also known as Parkinson's syndrome or PD, counts among the chronic diseases which are still incurable. The course of the disease is characterized by dying neurons in the brain. Predominantly such neurons substantia nigra, literally "black substance", neurons are affected which contain the neurotransmitter dopamine. Therefore, the formation of the neurotransmitter dopamine to a sufficient extent is no longer ensured. Changes (i.e. Lewy bodies, dying of other neuron types) can be found also in other parts of the brain, i.e. in the nucleus coeruleus, the Raphe nuclei, the Nucleus Basalis of Meynert, the nucleus of the vagus nerve and the hippocampus. Dopamine is a neurotransmitter essential for the control of the locomotor system; its lack leads to movement disorders such as trembling (resting tremor), involuntary muscular rigidity (rigor) and a deceleration of movement (hypokinesia). In advanced stades further movement disorders occur such as the inability to initiate a movement (freezing) and the incapability of maintaining an upright posture with the risk of falling. Further, cogitation, memory and the circulatory control are affected and feelings change involving depressions and at the final stage dementia.

Parkinson's disease is divided into a sporadic form (about 95% of the affected) and a familial form. In the latter, the main cause is the inheritance of the disease risk. Besides, many diseases are described in which movement disorders occur, but their ethology is based on other causes. They are referred to as secondary parkinsonism. These forms can be caused by drugs such as neuroleptics and reserpine and its derivatives. In addition, a hemiparkinsonism hemiatrophy syndrome is known. A Parkinson's syndrome is also described for hydrocephalus, oxygen deficiency, cerebral infections (encephalitis), manganese intoxications, carbon monoxide (CO), 1-methyl-4-phenyl-1,2,3,6-tetrahydropyridine (MPTP) and cyanide. Further causes are parathyroid diseases, a brain tumor, a brain lesion and multiple occlusions (infarctions) of cerebral vessels. Further diseases involving movement disorders are Alzheimer's disease, diffuse Lewy bodies disease, frontotemporal dementia, Lytico-Bodig disease (Parkinsonism-dementia-amyotrophic lateral sclerosis), striatonigral degeneration, sporadic olivo-ponto-cerebellar degeneration, progressive pallidal atrophy, progressive supranuclear palsy, Huntington's disease, X chromosome-linked dystonia (Lubag disease), mitochondrial cytopathy with striatal necrosis, neuroacanthocytosis and Wilson's disease. A reduced function of dopaminergic neurons is also involved in the so-called restless legs syndrome.

Currently, the dopamine precursor L-DOPA is applied for compensating the lack of dopamine and drugs are used which directly stimulate dopamine receptors as well as drugs which inhibit the degradation of dopamine. However, soon there occurred side effects of a long-term treatment with L-DOPA which range from dyskinesia (abnormal, involuntary movements) to dystonia (painful muscular cramps) and abrupt alternating movement-freezing-stages. Moreover, it was recognized that L-DOPA can lead to an accelerated loss of dopaminergic neurons in the brain.

In Germany, one to two percent of the people over 60 years suffer from Parkinson's disease. Thus, there is the urgent need to provide drugs which are suitable for the treatment of Parkinson's disease and other movement disorders, particularly well-tolerated substances and pharmaceutical formulations which can be used for prophylaxis and treatment of neurodegenerative diseases and movement disorders.

SUMMARY OF THE INVENTION

The compounds according to the invention shall be used in particular in Parkinson's disease. This problem is solved by the technical teachings of the independent claims. Further beneficial embodiments, aspects and details of the invention result from the dependent claims, the description and the examples.

One embodiment is directed to compounds of the general formula (I)

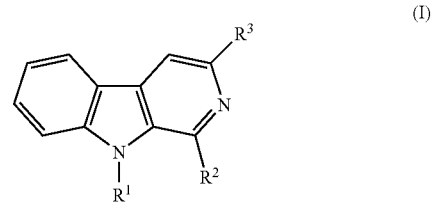

wherein
$R^1$ stands for one of the following moieties:
—$R^{16}$, —$CR^4R^5R^6$, —X—$CR^4R^5R^6$, —X—$R^4$, —CO—NH—$R^{16}$, —CO—O—$R^{16}$;
$R^2$ and $R^3$ mean the following moieties independent from one another: —H, —$R^7$, —$R^8$, —$CR^9R^{10}R^{11}$, —$CR^{12}R^{13}R^{14}$, —Y—$CR^9R^{10}R^{11}$, —Z—$CR^{12}R^{13}R^{14}$, —Y—$R^{15}$, —Z—$R^{15}$, —O—$R^{17}$, —S—$R^{18}$, —NH—$R^{19}$, —CO—NH—$R^{20}$, —CO—O—$R^{21}$;
X can be selected from —(CH$_2$)$_n$—, —CH═CH—, —C═O—, —CH$_2$—CO—, —CO—, —CO—CH$_2$;
Y, Z mean independent from one another: —(CH$_2$)$_m$—, —CH═CH—, —C═C—, —O—(CH$_2$)$_p$—, —NH—(CH$_2$)$_q$—, —NH—CO—, —CO—, —O—CO—;
m, p, q represent an integer between 1 and 4 independent from one another;
n represents an integer between 1 and 6
$R^4$-$R^{15}$ mean the following moieties independent from one another: —H, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OPh, —OCH$_2$-Ph, —OCPh$_3$, —SH, —SCH$_3$, —SC$_2$H$_5$, —SC$_3$H$_7$, —S-cyclo-C$_3$H$_5$, —SCH(CH$_3$)$_2$, —SC(CH$_3$)$_3$, —NO$_2$, —F, —Cl, —Br, —I, —N$_3$, —CN, —OCN, —NCO, —SCN, —NCS, —CHO, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, —COCN, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —OOC—CH$_3$, —OOC—C$_2$H$_5$, —OOC—C$_3$H$_7$, —OOC-cyclo-C$_3$H$_5$, —OOC—CH(CH$_3$)$_2$, —OOC—C(CH$_3$)$_3$, —CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON(cyclo-C$_3$H$_5$)$_2$, —CON[CH(CH$_3$)$_2$]$_2$, —CON[C(CH$_3$)$_3$]$_2$, —NHCOCH$_3$, —NHCOC$_2$H$_5$, —NHCOC$_3$H$_7$, —NHCO-cyclo-C$_3$H$_5$, —NHCO—CH(CH$_3$)$_2$, —NHCO—C(CH$_3$)$_3$, —NHCO—OCH$_3$, —NHCO—OC$_2$H$_5$, —NHCO—OC$_3$H$_7$, —NHCO—O-cyclo-C$_3$H$_5$, —NHCO—OCH(CH$_3$)$_2$, —NHCO—OC(CH$_3$)$_3$, —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —N[C(CH$_3$)$_3$]$_2$, —SOCH$_3$, —SOC$_2$H$_5$, —SOC$_3$H$_7$, —SO-cyclo-C$_3$H$_5$, —SOCH(CH$_3$)$_2$, —SOC(CH$_3$)$_3$, —SO$_2$CH$_3$, —SO$_2$C$_2$H$_5$, —SO$_2$C$_3$H$_7$, —SO$_2$-cyclo-C$_3$H$_5$, —SO$_2$CH(CH$_3$)$_2$, —SO$_2$C(CH$_3$)$_3$, —SO$_3$H, —SO$_3$CH$_3$, —SO$_3$C$_2$H$_5$, —SO$_3$C$_3$H$_7$, —SO$_3$-cyclo-C$_3$H$_5$, —SO$_3$CH(CH$_3$)$_2$, —SO$_3$C(CH$_3$)$_3$, —OCF$_3$, —OC$_2$F$_5$, —O—COOCH$_3$, —O—COOC$_2$H$_5$, —O—COOC$_3$H$_7$, —O—COO-cyclo-C$_3$H$_5$, —O—COOCH(CH$_3$)$_2$, —O—COOC(CH$_3$)$_3$, —NH—CO—NH$_2$, —NH—CO—NHCH$_3$, —NH—CO—NHC$_2$H$_5$, —NH—CO—NHC$_3$H$_7$, —NH—CO—NH-cyclo-C$_3$H$_5$, —NH—CO—NH[CH(CH$_3$)$_2$], —NH—CO—NH[C(CH$_3$)$_3$], —NH—CO—N(CH$_3$)$_2$, —NH—CO—N(C$_2$H$_5$)$_2$, —NH—CO—N(C$_3$H$_7$)$_2$, —NH—CO—N(cyclo-C$_3$H$_5$)$_2$, —NH—CO—N[CH(CH$_3$)$_2$]$_2$, —NH—CO—N[C(CH$_3$)$_3$]$_2$, —NH—CS—NH$_2$, —NH—CS—NHCH$_3$, —NH—CS—NHC$_2$H$_5$, —NH—CS—NHC$_3$H$_7$, —NH—CS—NH-cyclo-C$_3$H$_5$, —NH—CS—NH[CH(CH$_3$)$_2$], —NH—CS—NH[C(CH$_3$)$_3$], —NH—CS—N(CH$_3$)$_2$, —NH—CS—N(C$_2$H$_5$)$_2$, —NH—CS—N(C$_3$H$_7$)$_2$, —NH—CS—N(cyclo-C$_3$H$_5$)$_2$, —NH—CS—N[CH(CH$_3$)$_2$]$_2$, —NH—CS—N[C(CH$_3$)$_3$]$_2$, —NH—C(=NH)—NH$_2$, —NH—C(=NH)—NHCH$_3$, —NH—C(=NH)—NHC$_2$H$_5$, —NH—C(=NH)—NHC$_3$H$_7$, —OC$_6$H$_4$—OCH$_3$, —NH—C(=NH)—NH-cyclo-C$_3$H$_5$, —NH—C(=NH)—NH[CH(CH$_3$)$_2$], —CF$_2$Cl, —NH—C(=NH)—NH[C(CH$_3$)$_3$], —NH—C(=NH)—N(CH$_3$)$_2$, —NH—C(=NH)—N(C$_2$H$_5$)$_2$, —NH—C(=NH)—N(C$_3$H$_7$)$_2$, —NH—C(=NH)—N(cyclo-C$_3$H$_5$)$_2$, —OC$_6$H$_4$—CH$_3$, —NH—C(=NH)—N[CH(CH$_3$)$_2$]$_2$, —NH—C(=NH)—N[C(CH$_3$)$_3$]$_2$, —O—CO—NH$_2$, —O—CO—NHCH$_3$, —O—CO—NHC$_2$H$_5$, —O—CO—NHC$_3$H$_7$, —O—CO—NH-cyclo-C$_3$H$_5$, —O—CO—NH[CH(CH$_3$)$_2$], —O—CO—NH[C(CH$_3$)$_3$], —O—CO—N(CH$_3$)$_2$, —O—CO—N(C$_2$H$_5$)$_2$, —O—CO—N(C$_3$H$_7$)$_2$, —O—CO—N(cyclo-C$_3$H$_5$)$_2$, —O—CO—N[CH(CH$_3$)$_2$]$_2$, —O—CO—N[C(CH$_3$)$_3$]$_2$, —O—CO—OCH$_3$, —O—CO—OC$_2$H$_5$, —O—CO—OC$_3$H$_7$, —O—CO—O-cyclo-C$_3$H$_5$, —O—CO—OCH(CH$_3$)$_2$, —O—CO—OC(CH$_3$)$_3$.

$R^4$-$R^{21}$ mean the following moieties independent from one another:

—CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, cyclo-C$_3$H$_5$, cyclo-C$_4$H$_7$, cyclo-C$_5$H$_9$, cyclo-C$_6$H$_{11}$, cyclo-C$_7$H$_{13}$, cyclo-C$_8$H$_{15}$, -Ph, —CH$_2$-Ph, —CPh$_3$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH=CH$_2$, —CH$_2$—CH=CH$_2$, —C(CH$_3$)=CH$_2$, —CH=CH—CH$_3$, —C$_2$H$_4$—CH=CH$_2$, —C$_7$H$_{15}$, —C$_8$H$_{17}$, —CH$_2$—CH=CH—CH$_3$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH$_2$—CH$_3$, —C$_3$H$_6$—CH=CH$_2$, —C$_2$H$_4$—CH=CH—CH$_3$, —CH$_2$—CH=CH—C$_2$H$_5$, —CH=CH—C$_3$H$_7$, —CH$_2$—CH=CH—CH=CH$_2$, —CH=CH—CH=CH—CH$_3$, —CH$_2$—CH=C(CH$_3$)—CH=CH$_2$, —CH=CH—CH=C(CH$_3$)—CH$_3$, —C(CH$_3$)=CH—CH=CH$_2$, —CH=CH—CH$_2$, —CH=CH—C—C(CH$_3$)=CH$_2$, —C$_2$H$_4$—C(CH$_3$)=CH$_2$, —CH$_2$—CH(CH$_3$)—CH=CH$_2$, —CH(CH$_3$)—CH$_2$—CH=CH$_2$, —CH$_2$—CH=C(CH$_3$)$_2$, —CH$_2$—C(CH$_3$)=CH—CH$_3$, —CH(CH$_3$)—CH=CH—CH$_3$, —CH=CH—CH(CH$_3$)$_2$, —CH=C(CH$_3$)—C$_2$H$_5$, —C(CH$_3$)=CH—C$_2$H$_5$, —C(CH$_3$)=C(CH$_3$)$_2$, —C(CH$_3$)$_2$—CH=CH$_2$, —CH(CH$_3$)—C(CH$_3$)=CH$_2$, —C(CH$_3$)=CH—CH=CH$_2$, —CH=C(CH$_3$)—CH=CH$_2$, —CH=CH—C(CH$_3$)=CH$_2$, —C$_4$H$_8$—CH=CH$_2$, —C$_3$H$_6$—CH=CH—CH$_3$, —C$_2$H$_4$—CH=CH—C$_2$H$_5$, —CH$_2$—CH=CH—C$_3$H$_7$, —CH=CH—C$_4$H$_9$, —C$_3$H$_6$—C(CH$_3$)=CH$_2$, —CH$_2$—CH$_2$—CH$_2$—OCH$_3$, —C$_2$H$_4$—CH(CH$_3$)—CH=CH$_2$, —CH$_2$—CH(CH$_3$)—CH$_2$—CH=CH$_2$, —CH$_2$NH$_2$, —CH(CH$_3$)—C$_2$H$_4$—CH=CH$_2$, —C$_2$H$_4$—CH=C(CH$_3$)$_2$, —C$_2$H$_4$—C(CH$_3$)=CH—CH$_3$, —CH$_2$—CH(CH$_3$)—CH=CH—CH$_3$, —CH(CH$_3$)—CH$_2$—CH=CH—CH$_3$, —CH$_2$OH, —CH$_2$SH, —CH$_2$—CH=CH—CH(CH$_3$)$_2$, —CH$_2$—CH=C(CH$_3$)—C$_2$H$_5$, —CH$_2$—CH$_2$—CH$_2$NH$_2$, —CH$_2$—C(CH$_3$)=CH—C$_2$H$_5$, —CH(CH$_3$)—CH=CH—C$_2$H$_5$, —CH$_2$—CH$_2$NH$_2$, —CH=CH—CH$_2$—CH(CH$_3$)$_2$, —CH=CH—CH(CH$_3$)—C$_2$H$_5$, —CH=C(CH$_3$)—C$_3$H$_7$, —C(CH$_3$)=CH—C$_3$H$_7$, —C(CH$_3$)=CH—C(CH$_3$)=CH$_2$, —CH$_2$—CH$_2$SH, —CH(CH$_3$)—C(CH$_3$)=CH$_2$, —CH(CH$_3$)—CH(CH$_3$)—CH=CH$_2$, —CH$_2$—CH$_2$—CH$_2$OH, —CH$_2$—C(CH$_3$)$_2$—CH=CH$_2$, —C(CH$_3$)$_2$—CH$_2$—CH=CH$_2$, —CH$_2$—C(CH$_3$)=C(CH$_3$)$_2$, —CH(CH$_3$)—CH=C(CH$_3$)$_2$, —C(CH$_3$)$_2$—CH=CH—CH$_3$, —CH$_2$—CH$_2$—CH$_2$SH, —CH(CH$_3$)—C(CH$_3$)=CH—CH$_3$, —CH=C(CH$_3$)—CH(CH$_3$)$_2$, —C(CH$_3$)=CH—CH(CH$_3$)$_2$, —C(CH$_3$)=C(CH$_3$)—C$_2$H$_5$, —CH=CH—C(CH$_3$)$_3$, —C(CH$_3$)$_2$—C(CH$_3$)=CH$_2$, —CH(C$_2$H$_5$)—C(CH$_3$)=CH$_2$, —C(CH$_3$)(C$_2$H$_5$)—CH=CH$_2$, —CH(CH$_3$)—C(C$_2$H$_5$)=CH$_2$, —CH$_2$—C(C$_3$H$_7$)=CH$_2$, —CH$_2$—C(C$_2$H$_5$)=CH—CH$_3$, —CH(C$_2$H$_5$)—CH=CH—CH$_3$, —C(C$_4$H$_9$)=CH$_2$, —C(C$_3$H$_7$)=CH—CH$_3$, —C(C$_2$H$_5$)=CH—C$_2$H$_5$, —C(C$_2$H$_5$)=C(CH$_3$)$_2$, —C[C(CH$_3$)$_3$]=CH$_2$, —C[CH(CH$_3$)(C$_2$H$_5$)]=CH$_2$, —C[CH$_2$—CH(CH$_3$)$_2$]=CH$_2$, —C$_2$H$_4$—CH=CH—CH=CH$_2$, —C$_6$H$_4$—OCH$_3$, —CH$_2$—CH=CH—CH$_2$—CH=CH$_2$, —CH=CH—C$_2$H$_4$—CH=CH$_2$, —C$_6$H$_4$—OH, —CH$_2$—CH=CH—CH=CH—CH$_3$, —CH=CH—CH$_2$—CH=CH—CH$_3$, —CH=CH—CH=CH—CH$_3$, —CH$_2$—CH$_2$—OCH$_3$, —CH=CH—CH=CH—C$_2$H$_5$, —CH$_2$—CH=CH—C(CH$_3$)=CH$_2$, —CH$_2$—CH$_2$OH, —CH$_2$—CH=C(CH$_3$)—CH=CH$_2$, —CH$_2$—C(CH$_3$)=CH—CH=CH$_2$, —CH$_2$—OCH$_3$, —CH(CH$_3$)—CH=CH—CH=CH$_2$, —CH=CH—CH$_2$—C(CH$_3$)=CH$_2$, —CH=CH—CH(CH$_3$)—CH=CH$_2$, —CH=C(CH$_3$)—CH$_2$—CH=CH$_2$, —C(CH$_3$)=CH—CH$_2$—CH=CH$_2$, —CH=CH—CH=C(CH$_3$)$_2$, —CH$_2$—C$_6$H$_4$—OCH$_3$, —CH=CH—C(CH$_3$)=CH—CH$_3$, —CH=C(CH$_3$)—CH=CH—CH$_3$, —CH$_2$—C$_6$H$_4$—OH, —C(CH$_3$)=CH—CH=CH—CH$_3$, —CH=C(CH$_3$)—C(CH$_3$)=CH$_2$, —C(CH$_3$)=CH—C(CH$_3$)=CH$_2$, —C(CH$_3$)=C(CH$_3$)—CH=CH$_2$, —CH=CH—CH=CH—CH=CH$_2$, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —C$_3$H$_6$—C≡CH, —C$_2$H$_4$—C≡C—CH$_3$, —CH$_2$—C≡C—C$_2$H$_5$, —C≡C—C$_3$H$_7$, —CH(CH$_3$)—C≡CH, —CH$_2$—CH(CH$_3$)—C≡CH, —CH(CH$_3$)—CH$_2$—C≡CH, —CH(CH$_3$)—C≡C—CH$_3$, —C$_4$H$_8$—C≡CH, —C$_3$H$_6$—C≡C—CH$_3$, —C$_2$H$_4$—C≡C—C$_2$H$_5$, —CH$_2$—C≡C—C$_3$H$_7$, —C≡C—C$_4$H$_9$, —C≡C—C(CH$_3$)$_3$, —C$_2$H$_4$—CH(CH$_3$)—C≡CH, —CH$_2$—CH(CH$_3$)—CH$_2$—C≡CH, —CH$_2$—C≡C—CH(CH$_3$)$_2$, —CH(CH$_3$)—C$_2$H$_4$—C≡CH, —CH$_2$—CH(CH$_3$)—C≡C—CH$_3$, —CH(CH$_3$)—CH$_2$—C≡C—CH$_3$, —CH(CH$_3$)—C≡C—C$_2$H$_5$, —C≡C—CH(CH$_3$)—C$_2$H$_5$, —C≡C—CH$_2$—CH(CH$_3$)$_2$, —CH(C$_2$H$_5$)—C≡C—CH$_3$, —C(CH$_3$)$_2$—C≡C—CH$_3$, —CH(C$_2$H$_5$)—CH$_2$—C≡CH, —CH$_2$—CH(C$_2$H$_5$)—C≡CH, —C(CH$_3$)$_2$—CH$_2$—C≡CH, —CH$_2$—C(CH$_3$)$_2$—C≡CH, —CH(CH$_3$)—CH(CH$_3$)—C≡CH, —CH(C$_3$H$_7$)—C≡CH, —C(CH$_3$)(C$_2$H$_5$)—C≡CH, —C≡C—C≡CH, —CH$_2$—C≡C—C≡CH, —C≡C—C≡C—CH$_3$, —CH(C≡CH)$_2$, —C$_2$H$_4$—C≡C—C≡CH, —CH$_2$—C≡C—CH$_2$—C≡CH, —C≡C—C$_2$H$_4$—C≡CH, —CH$_2$—C≡C—C≡C—CH$_3$, —C≡C—CH$_2$—C≡C—CH$_3$, —C≡C—C≡C—C$_2$H$_5$, —C≡C—CH(CH$_3$)—C≡CH, —CH(CH$_3$)—C≡C—C≡CH, —CH(C≡CH)—CH$_2$—C≡CH, —C(C≡CH)$_2$—CH$_3$, —CH$_2$—CH(C≡CH)$_2$, —CH(C≡CH)—C≡C—CH$_3$;

and pharmaceutically acceptable salts, solvates, hydrates, complex compounds, enantiomers, diastereomers, mixtures of diastereomers, prodrugs, tautomers and racemates of the aforementioned compounds.

The herein used expression prodrug is defined as a pharmacologic substance which is administered in an inactive or less effective form. After administration, it shall be metabolized in the body into its active, effective form.

The herein used expression tautomer is defined as an organic substance which can be transferred by a chemical reaction, the tautomerization, into its equilibrium isomer. The tautomerization can preferably be catalyzed by bases, acids or other suitable substances.

General Synthesis of 9-Alkyl-β-carbolines

The lead compound norharman can be produced according to procedures known from literature, as for example described in example 9.

N-alkylation in position 9 occurs according to conventional alkylation reactions by means of alkyl iodides, alkyl bromides, alkyl chlorides, alkyl mesylates, alkyl tosylates or other alkylation reagents according to the following reaction scheme:

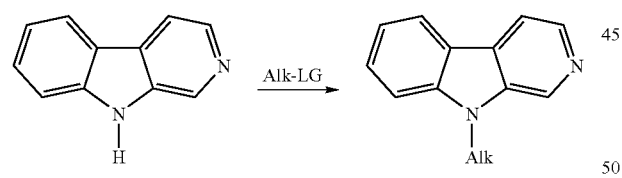

LG stands for the leaving group. The alkylation reactions are preferably base-catalyzed.

General Reaction Protocol for the Alkylation:

1 mol equivalent norharman is dissolved in a dried solvent such as DMF, THF, methylene chloride etc. under protective gas. Deprotonation occurs through excess of a strong base, preferably sodium hydride (about 2 mol equivalent) at reduced temperature (0° C. to −78° C.). Also at a temperature below 0° C., 1.0 to 1.2 mol equivalent of an alkylating agent are added which can be dissolved in a dried solvent. The mixture is stirred overnight whereas the reaction solution can heat up to room temperature. Processing occurs in a manner known to a person skilled in the art. Not transformed Norharman can be removed through ion exchange chromatography or ion pair extraction. In general, yields of 30 to 75% of the theory are achieved.

The following compounds were produced according to the aforementioned alkylation.

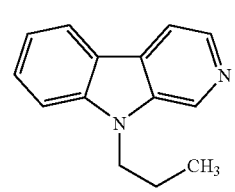
compound A

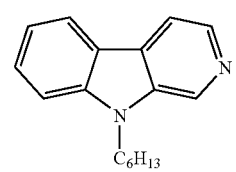
compound B

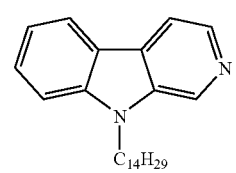
compound C

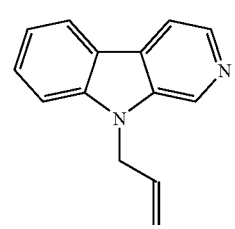
compound D

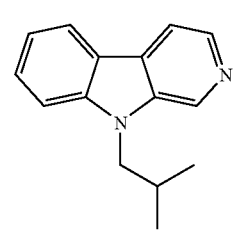
compound E

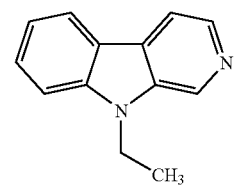
compound F

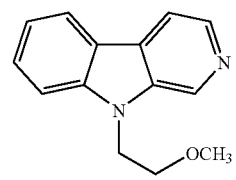
compound G

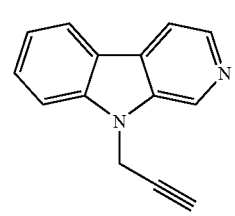
compound H compound I

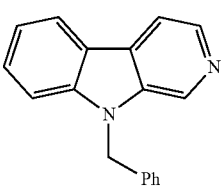

compound J

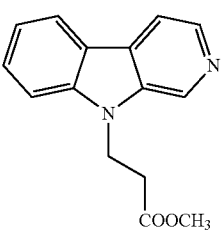

compound K

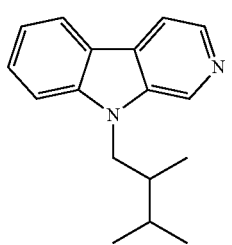

compound L

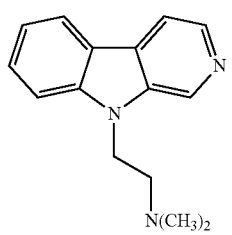

General Synthesis of 1,3-disubstituted β-carbolines

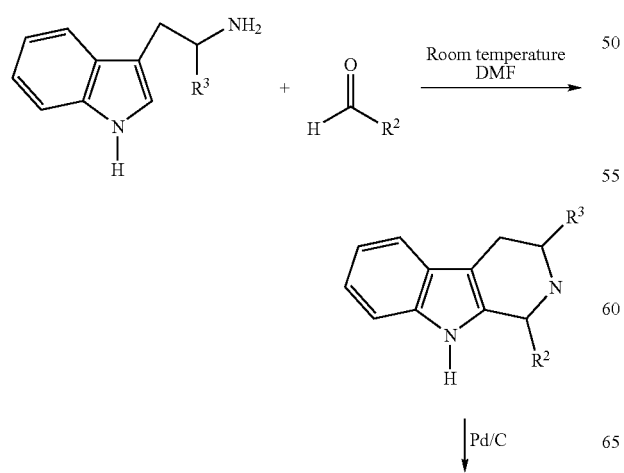

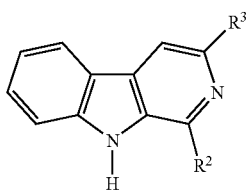

To obtain 1,3-disubstituted, indol derivates were reacted with the respective aldehydes according to the aforementioned reaction scheme.

Thereby 0.1 mol of the indol derivative were dissolved in DMF and 0.12 mol of the aldehyde was added while stirring. The reaction mixture was stirred for 16 hours at room temperature. After removing the solvent, the resulting solid was recrystallized twice in toluene and dried. In a further step of the synthesis 0.07 mol of the solid recrystallized in toluene and dried was dissolved in 600 ml cumene and heated with 2.6 g Pd/C (10%) for 90 minutes at reflux under nitrogen atmosphere. After adding 100 ml ethanol the heated solution was filtered and the carbon was extracted with 3×30 ml heated ethanol. The combined liquid fractions were removed from the solvent under vacuum and the residue crystallized out of toluene in order to obtain the 1,3-disubstituted norharman derivative.

The respective 1-substituted β-carbolines are obtained if $R^3$ is a hydrogen atom.

After the ring closure reaction N-alkylation at position 9 will be carried out by means of a base, preferably a hydride, and the subsequent addition of an alkylating agent, i.e. an alkyl iodide. A detailed procedure is given in the experimental part. According to this procedure the following compounds were produced.

Preferred are the following compounds of the general formulas (II)-(V)

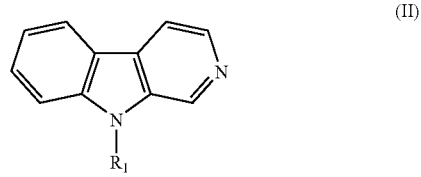
(II)

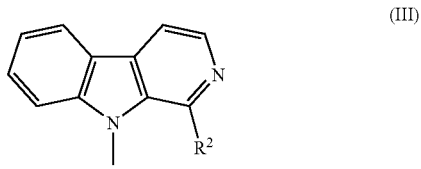
(III)

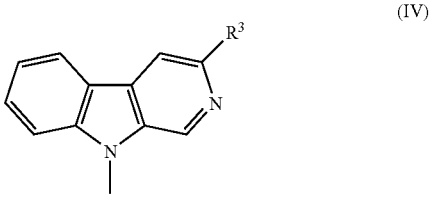
(IV)

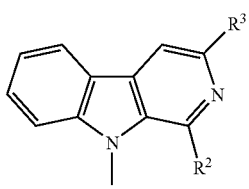

(V)

The inventive 9-Alkyl-β-carbolines surprisingly show neuroprotective effect and promote the growth of new and functional dopaminergic neurons.

Substituents at positions 9 ($R^1$), 1 ($R^2$) and 3 ($R^3$) of the β-carboline ring system are preferred. The substitution pattern in $R^1$ preferably includes alkyl substituents, in particular preferred is the methyl substituent. It is particularly preferred that the rests $R^2$ and $R^3$ include alkyl substituents, halogens and alkoxy substituents.

Particularly preferred compounds accordingly are:

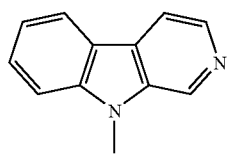

(VI)

9-methyl-9H-β-carboline

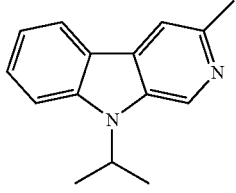

(VII)

9-iso-propyl-9H-β-carboline

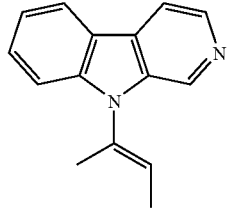

(VIII)

9-[(1Z)-1-methylprop-1-enyl]-9H-β-carboline

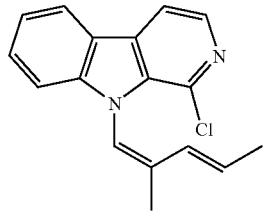

(IX)

1-chloro-9-[1Z,3E)-2-methylpenta-1,3-dienyl]-9H-β-carboline

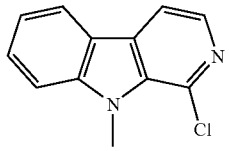

(X)

1-chloro-9-methyl-9H-β-carboline

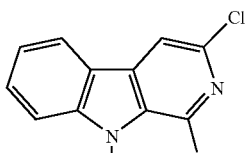

(XI)

1,3-dichloro-9-methyl-9H-β-carboline

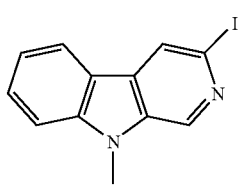

(XII)

3-iodo-9-methyl-9H-β-carboline

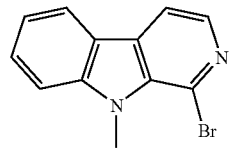

(XIII)

1-bromo-9-methyl-9H-β-carboline

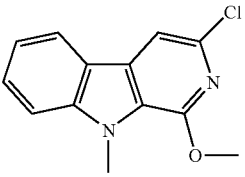

(XIV)

1-methoxy-3-chloro-9-methyl-9H-β-carboline

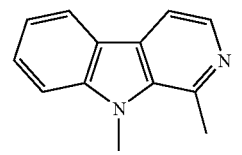

(XV)

1,9-dimethyl-9H-β-carboline

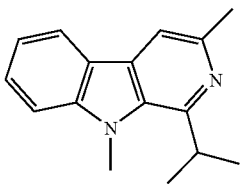

(XVI)

1-isopropyl-3,9-dimethyl-9H-β-carboline

-continued (XVII)

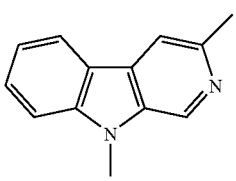

3,9-dimethyl-9H-β-
carboline (XVIII)

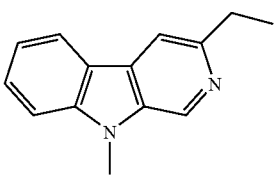

3-ethyl-9-methyl-9H-β-
carboline (IXX)

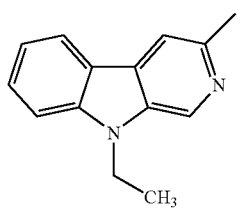

9-ethyl-3-methyl-9H-β-
carboline (XX)

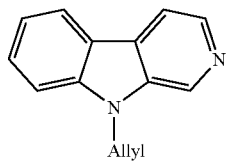

9-allyl-3-isopropyl-9H-β-
carboline

Therefore, the compounds described herein and in particular the preferred compounds of the general formula (II)-(XX) can be used for the production of a pharmaceutical formulation for the treatment and/or prophylaxis of movement disorders, movement disorders due to other causes than Parkinson's disease, neurodegenerative diseases, Alzheimer's disease, Parkinson's disease, hemiparkinsonism hemiatrophy syndrome, Parkinson's syndrome due to or together with hydrocephalus, oxygen deficiency, cerebral infections (encephalitis), manganese intoxication, carbon monoxide (CO), 1-methyl-4-phenyl-1,2,3,6-tetrahydropyridine (MPTP) and cyanide, parathyroid diseases, brain tumor, brain lesion, cerebral infarctions, Lewy bodies disease, frontotemporal dementia, Lytico-Bodig disease (Parkinsonism-dementia-amyotrophic lateral sclerosis), striatonigral degeneration, Shy-Drager syndrome, sporadic olivo-ponto-cerebellar degeneration, progressive pallidal atrophy, progressive supranuclear palsy, Hallervorden-Spatz syndrome, Huntington's disease, X chromosome-linked dystonia (Lubag disease), mitochondrial cytopathy with striatal necrosis, neuroacanthocytosis and Wilson's disease.

The term movement disorders refers particularly to spastic disorders, hyperkinesias, dystonias, athetoses, dyskinesias, myoclonus syndromes, Wilson's disease, choreatic syndromes, tics, Tourette disorders, ballism, tremor syndromes and Parkinson's disease.

The compounds can be administered eo ipso or in form of a pharmacologically effective salt. Since the compounds have basic properties, salts of these compounds can be produced according to conventional methods.

As acids which create an acid addition salt with the compounds, the following can be mentioned: sulfuric acid, sulfonic acid, phosphoric acid, nitric acid, nitrous acid, perchloric acid, hydrobromic acid, hydrochloric acid, formic acid, acetic acid, propionic acid, succinic acid, oxalic acid, gluconic acid glycons, dextronic acid), lactic acid, malic acid, tartaric acid, tartronic acid (hydroxyl malonic acid, hydroxyl propane diacid), fumaric acid, citric acid, ascorbic acid, maleic acid, malonic acid, hydroxyl maleic acid, pyruvic acid, phenylacetic acid, (o-, m-, p-)methylbenzoic acid, benzoic acid, p-aminobenzoic acid, p-hydroxybenzoic acid, salicylic acid, p-amino-salicylic acid methanesulfonic acid, ethanesulfonic acid, hydroxyethanesulfonic acid, ethylenesulfonic acid, p-toluolsulfonic acid, naphthylsulfonic acid, naphthylaminesulfonic acid, sulfanilic acid, camphorsulfonic acid, quinic acid (quinine acid), o-methyl-mandelic acid, hydrogenbenzenesulfonic acid, picric acid (2,4,6-trinitrophenol), adipic acid, d-o-tolyl-tartaric acid, amino acids such as methionine, tryptophan, arginine and in particular acidic amino acids such as glutamic acid or aspartic acid.

Depending on the compound type betaine forms are possible also.

Further, the embodiments relate to pharmaceutical compositions which were produced using at least one inventive compound or a salt thereof.

Besides at least one compound, the pharmaceutical compositions contain a pharmaceutically acceptable carrier, excipient and/or solvent.

The pharmaceutical compositions can be produced and administered in form of a transdermal application system (patch, film), drops, mouth spray, nasal spray, pills, tablets, coated tablets, layered tablets, suppositories, gels, ointments, syrup, inhalation powders, granulates, emulsions, dispersions, microcapsules, capsules, powder or injection solutions. Moreover, the pharmaceutical compositions include formulations such as layered tablets for controlled and/or continuous release of the active agent and microencapsulations as specific dosage form.

Such formulations are, inter alia, suitable for inhalation or intraperitoneal, intramuscular, subcutaneous, mucocutaneous, oral, rectal, transdermal, topical, buccal, intradermal, intragastral, intracutaneous, intranasal, intrabuccal, percutaneous or sublingual administration.

For example, lactose, starch, sorbitol, sucrose, cellulose, magnesium stearate, dicalcium phosphate, calcium sulfate, talcum, mannitol, ethanol and the like can be used as pharmaceutically acceptable carrier. Powder and tablets can consist of such a carrier from 5 to 95%.

Moreover, starch, gelatine, natural sugars, natural and synthesized gums such as acacia gum or guar gum, sodium alginate, carboxymethyl cellulose, polyethylene glycol and waxes can be used as binder. Boric acid, sodium benzoate, sodium acetate, sodium chloride and the like can serve as lubricant.

Further, disintegrants, dyes, flavors and/or binders can be added to the pharmaceutical compositions.

Liquid formulations include solutions, suspensions, sprays and emulsions, for example water-based or water/propylene-glycol-based injection solutions for parenteral injections.

Low melting waxes, fatty acid esters and glycerides are preferred for the preparation of suppositories.

Capsules, for example, are produced from methyl cellulose, polyvinyl alcohols or denatured gelatine or starch.

Starch, sodium carboxymethyl starch, natural and synthesized gums such as carob bean gum, karaya, guar, tragacanth and agar as well as cellulose derivatives such as methyl cellulose, sodium carboxymethyl cellulose, microcrystalline cellulose such as alginates, aluminas and bentonites can be used as disintegrants. These components can be used in amounts of 2 to 30 percent by weight.

Sugar, starch from corn, rice or potatoes, natural gums such as acacia gum, gelatine, tragacanth, alginic acid, sodium alginate, ammonium calcium alginate, methyl cellulose, sodium carboxymethyl cellulose, hydroxypropylmethyl cellulose, polyvinyl pyrrolidone and inorganic compounds such as magnesium aluminum silicates can be added as binders. The binder can be added in amounts of 1 to 30 percent by weight.

Stearates such as magnesium stearate, calcium stearate, potassium stearate, stearic acid, high melting waxes and water-soluble lubricants such as sodium chloride, sodium benzoate, sodium acetate, sodium oleate, polyethylene glycol and amino acids such as leucine can be used as lubricants. Such lubricants can be used in amounts of 0.05 to 15 percent by weight.

Thus, the herein presented compounds are useful for the production of pharmaceutical formulations for the treatment of neurodegenerative diseases, Parkinson's disease and other movement disorders.

Another aspect is directed at the use of the compounds according to the general formula (I) for the acceleration of cell growth, in particular in (cell) culture media, growth media and fermentation media. For this purpose, at least one compound according to the general formula (I) or a physiologically acceptable salt thereof will be added to the medium as an additive in a concentration of 0.5 to 500 µM, preferably 1.0 to 250.0 µM, further preferred 10.0 µM to 100.0 µM and in particular preferred 40.0 µM to 60.0 µM.

Furthermore, embodiments include (cell) culture media, growth media and fermentation media which contain at least one compound according to the general formula (I), preferably in the above-mentioned concentration ranges.

The growth accelerating effect of the compounds according to the general formula (I) could be proven for many cell types as well as in human and animal cell cultures. Preferred cells are bone cells, cartilage cells, fibroblasts, neuronal cells, glial cells, dopaminergic cells, adipocytes, muscle cells, myocardial cells, dermal cells, hepatocytes, mesenchymal cells, gonadotropic cells, cumulus cells, blood cells, epithelium cells, endothelial cells, basal cells, adult and embryonic stem cells and multipotent precursor cells.

BRIEF DESCRIPTION OF THE DRAWINGS

Advantages of the present invention will become apparent to those skilled in the art with the benefit of the following detailed description of embodiments and upon reference to the accompanying drawings in which:

FIG. 1a Dose-dependent incubation of dopaminergic neurons for 48 hours (control).

FIG. 1b Dose-dependent incubation of dopaminergic neurons with 50 µM 9-methyl-β-carboline for 48 hours (DIV=Days in vitro).

FIG. 1c Percentage of dopaminergic neurons (dopamine neurons) after incubation with 10, 25, 50, 100, 200 µM 9-methyl-β-carboline for 48 hours from 10 DIV-12 DIV.

Figure 1D:
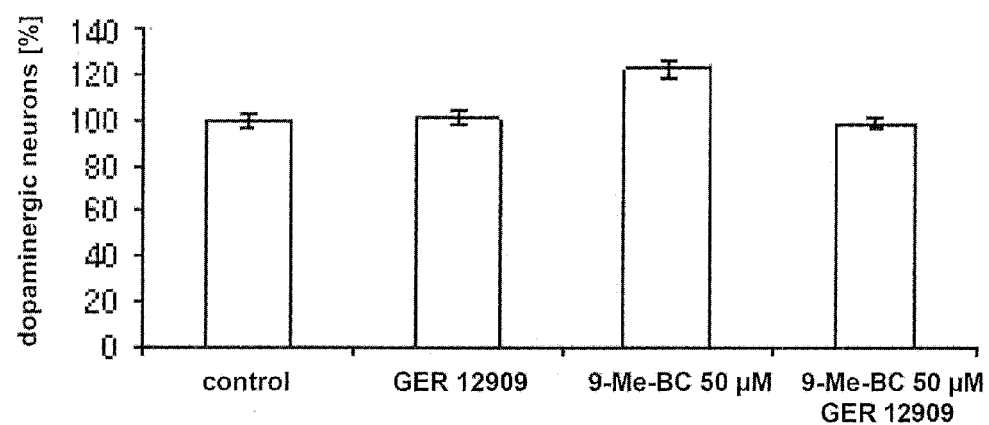
FIG. 1d Percentage of dopaminergic neurons after inactivation of the dopamine transporter DAT with GBR12909 after 48 hours. Influence of DAT-Inhibition with GBR12909 on the effect of 50 µM 9-Me-BC on the number of TH-positive neurons during a 48 hour incubation period.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

Example 1

For proving the effectiveness of the inventive 9-alkyl-β-carbolines experiments were carried out to find out which effects this compound class has on the formation of new dopaminergic neurons. As sample substance, 9-methyl-β-carboline (9-Me-BC) was selected.

The experiments were carried out with the human neuroblastoma cell line (SH-SY5Y-cells) and with a cell culture of primary nerve cells from the mice embryo midbrain. Herein it was found that 9-alkyl-β-carboline derivatives show a neuroprotective effect. Moreover, the mentioned compounds induce in the primary culture from the mice embryo midbrain the generation of new, differentiated and functional dopaminergic neurons.

To this aim midbrain cultures were prepared and kept for 10-12 days (DIV=Days in vitro) in an appropriate medium to accustom to in vitro conditions. Then 9-methyl-β-carboline was added in increasing concentrations and it was waited for 48 hours. Dopaminergic neurons were identified by staining with tyrosin hydroxylase. This enzyme occurs only in dopaminergic midbrain neurons. The number of dopaminergic neurons can be counted reliably with this method. In addition, hints can be obtained whether the dopaminergic neurons are mature or if they are precursor cells. The mature cells have characteristic extensions which also contain tyrosin hydroxylase.

Results:

The dopaminergic neurons exposed to 9-methyl-β-carboline for 48 hours had significantly more cellular extensions which were considerably more often branched than neurons without 9-methyl-β-carboline (FIG. 1a: control, FIG. 1b: 50 µM 9-methyl-β-carboline). Moreover, the number of dopaminergic neurons increased dose-dependently with a concentration up to ca. 100 µM (FIG. 1c). The effect of 9-methyl-β-carboline needs an intact function of the so-called dopamine transporter (DAT). Through selective inactivation of the transporter, i.e. by GBR12909, the increase in dopaminergic neurons does not occur (FIG. 1d). 9-methyl-β-carboline is also transported into the dopaminergic neurons via the DAT and only then can deploy its effect.

Example 2

Figure 2A:
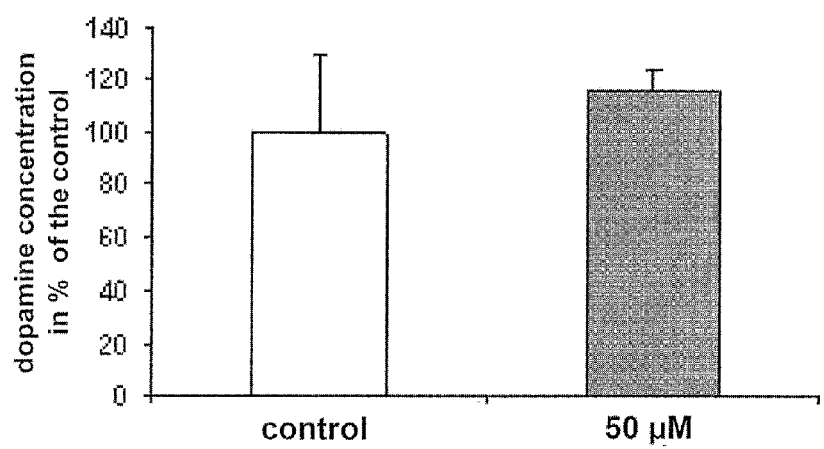
FIG. 2a Dopamine concentration (dopamine content) after incubation with 50 µM 9-methyl-β-carboline for 48 hours from 10 DIV-12 DIV.

To obtain further hints that the number of dopaminergic neurons really has increased, the dopamine concentration was measured. It slightly increased without reaching significance level (FIG. 2a). Another characteristic and specificity of dopaminergic neurons is the transport of dopamine into the neurons. Dopamine cannot permeate the outer membrane of neurons because of its hydrophilic character. It must be actively and energy-dependently transported through the DAT mechanism.

Results

Figure 2B:
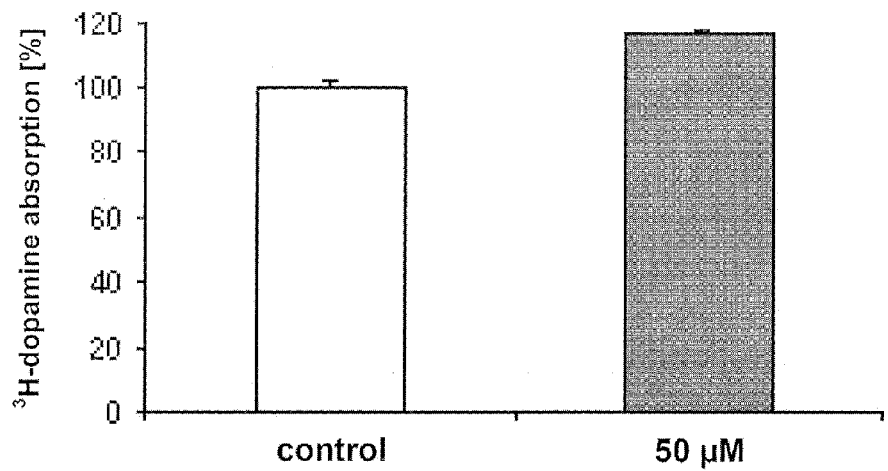
FIG. 2b Dopamine transport capacity of dopaminergic neurons after 48 hours. $^3$H-dopamine uptake after incubation with 50 µM 9-Me-BC for 48 hours from 10 DIV-12 DIV.

The neuronal transport capacity of dopamine increases in the culture containing 9-methyl-β-carboline (FIG. 2b). This is a strong hint towards a proliferation of functional dopaminergic neurons.

Example 3

9-methyl-β-carboline was used to show whether only dopaminergic neurons were influenced, or other neurons or glial cells as well. This question can be answered by the use of different dyes.

Figure 3:
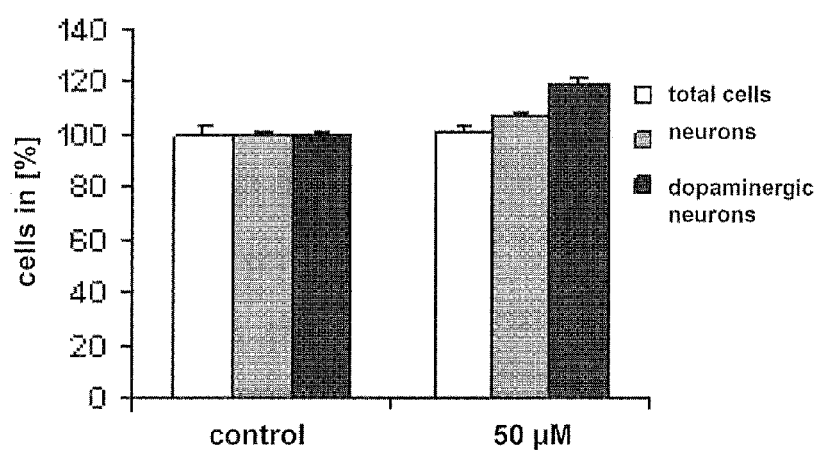
FIG. 3 Percentage of neurons (total) after incubation with 50 µM 9-methyl-β-carboline for 48 hours from 10 DIV-12 DIV.

As FIG. 3 shows, the total number of neurons increases, however, not that much as those of the dopaminergic neurons. Dopaminergic neurons thus are more sensitive to the effects of 9-methyl-β-carboline. But it can't be excluded that a longer exposition leads to a significant proliferation of other neuron types as well.

Example 4

Experiments at midbrain cells in culture were conducted with the question whether 9-methyl-β-carboline has a neuroprotective effect in general.

Figure 4A:
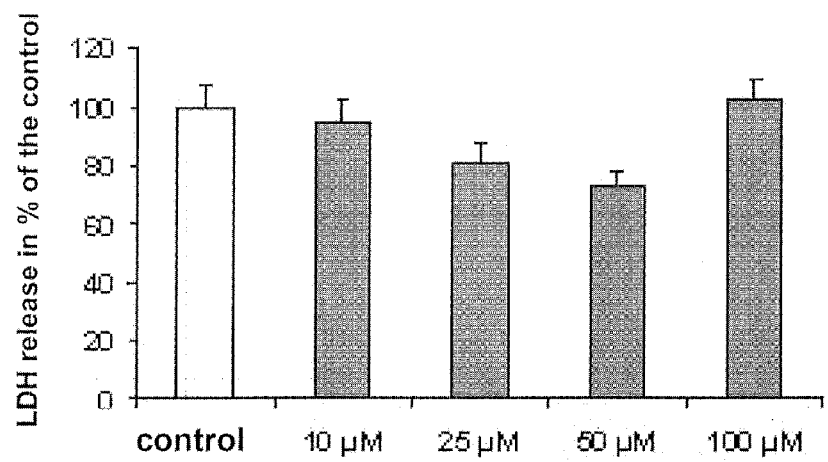
FIG. 4a LDH release after 48 hours of incubation with 50 µM 9-methyl-β-carboline for 48 hours 10 DIV-12 DIV.

Dying cells release the enzyme lactate dehydrogenase (LDH) into the medium. Since cells always die in culture always a small LDH concentration can be detected in the medium as an indirect measure for the vitality of the culture. Compared to control conditions the LDH concentration decreased after incubation with 9-methyl-β-carboline in a dose-dependent manner with a concentration up to 50 µM (FIG. 4a). The number of dead cells can be quantified by staining the cell nuclei with propidium iodide.

Results

Figure 4B:
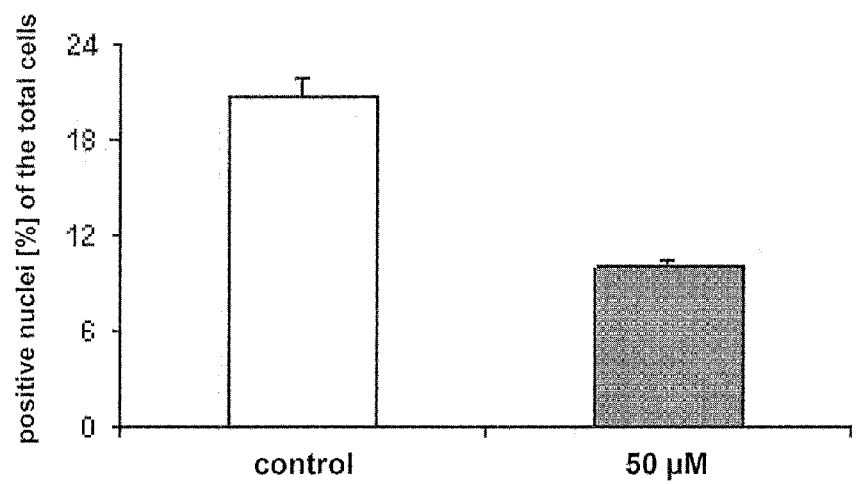
FIG. 4b Percentage of dead (necrotic) cells after incubation with 50 µM 9-methyl-β-carboline for 48 hours 10 DIV-12 DIV.
Figure 4C:
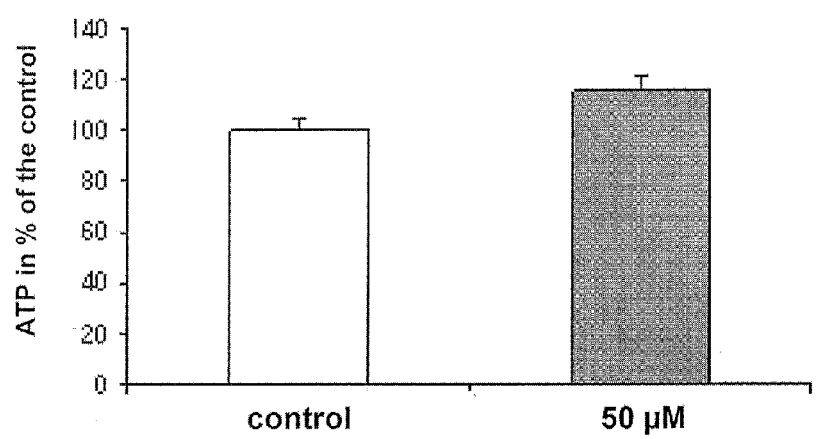
FIG. 4c ATP concentration (ATP content) after incubation with 50 µM 9-methyl-β-carboline (9-Me-BV) for 48 hours 10 DIV-12 DIV.
Figure 4D:
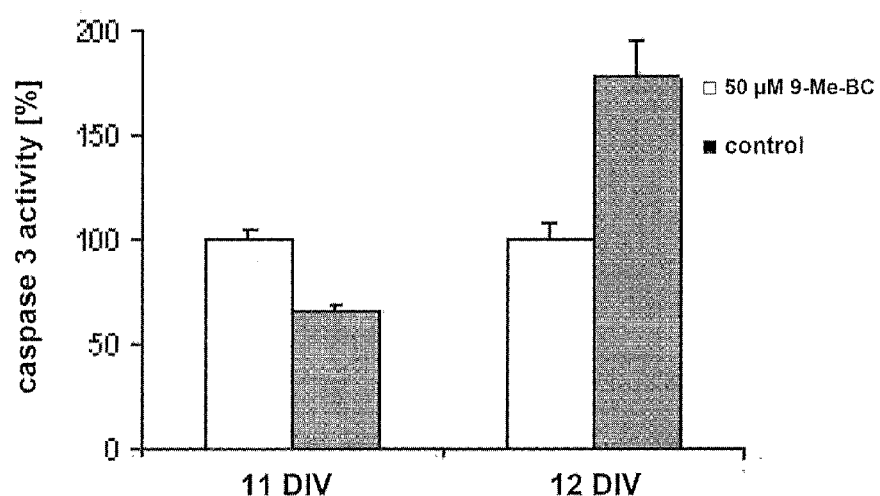
FIG. 4d Activity of the apoptosis enzyme caspase-3 during and after incubation with 50 µM 9-methyl-β-carboline for 48 hours 10 DIV-12 DIV.

In 48 hours about 20% of the cells in culture died. In cultures with a 9-Alkyl-β-carboline only about 10% of the cells died under the same conditions (FIG. 4b). Thus, the findings are in line with the LDH findings. ATP provides the cell with energy. Interestingly, the concentration of ATP increased in the cell culture with 9-Alkyl-β-carboline (FIG. 4c). The enzyme caspase-3 is an indicator for apoptosis. After 24 hours, the enzyme activity was reduced which hints at a reduction of apoptotic processes, after 48 hours, however, it was increased (FIG. 4d). The last finding hints at a switch of culture cells from reduced necrosis to apoptosis, thus a more precise regulation of cell death.

Example 5

The question whether 9-Alkyl-β-carboline derivatives lead to the differentiation of neurons is of outstanding importance. Hence, this question was examined in another model, namely human neuroblastoma cells.

Figure 6:
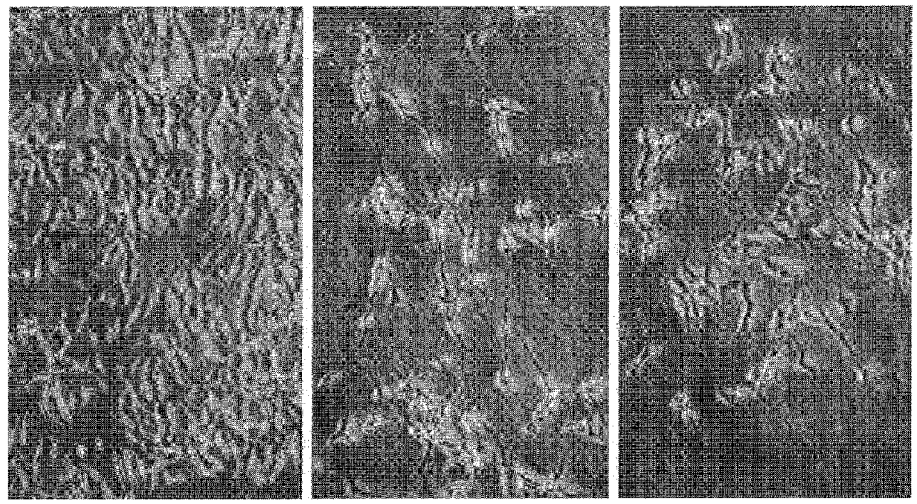
FIG. 6 Evidence of the reduction of cell proliferation by incorporation of bromodeoxyuridine into the cell nucleus chromatin.

This cell line has many characteristics which dopaminergic neurons have as well. The exposition of the cells to 9-methyl-β-carboline led to a growth of cellular extensions (FIG. 6). So this confirms the observations in the primary midbrain cultures that 9-methyl-β-carboline promotes the differentiation and thus the maturation of neuronal cells (FIG. 1a and FIG. 1b). FIG. 6 also shows that the cells exposed to 9-methyl-β-carboline proliferate less than control cells.

Results

Figure 5:
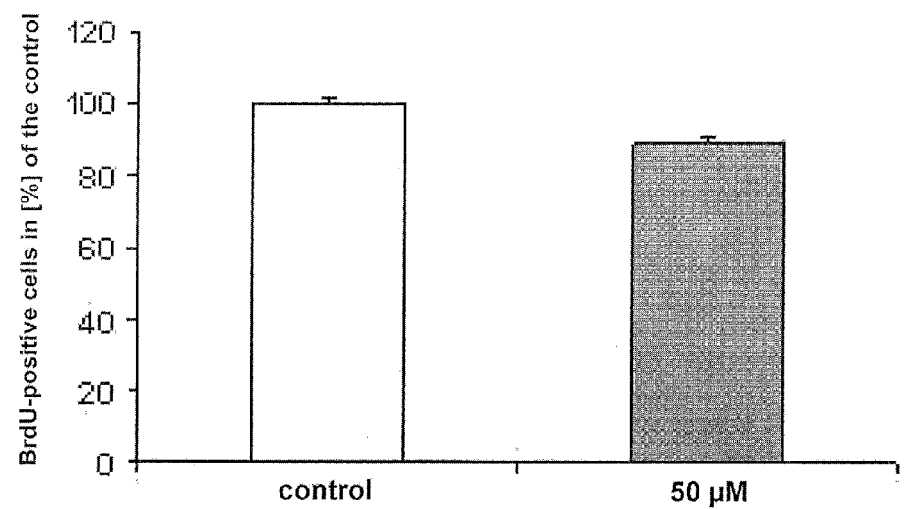
FIG. 5 Percentage of BrdU-positive cells of human neuroblastoma cells after incubation with 50 µM 9-methyl-β-carboline for 48 hours 10 DIV-12 DIV.

Most observations show that proliferation and differentiation are more or less mutually exclusive. Cell proliferation can be measured by the incorporation of bromodeoxyuridine. As shown in FIG. 5, the installation of bromodeoxyuridine into the chromatin in the cell nucleus decreases. This hints at a reduction of cell proliferation. This finding also supports the other findings that 9-alkyl-β-carboline derivatives promote cell differentiation.

Example 6

In another series of experiments it was investigated how the increase of dopaminergic neurons occurs.

Furthermore, the number of dead cells can be quantified by staining the cell nuclei.

This process hasn't been observed yet for any substance, least of all after an incubation time of only 48 hours. The importance of the observation is underlined by the fact that even after removing 9-Alkyl-β-carbolines the number of dopaminergic neurons still remains increased.

Figure 7:
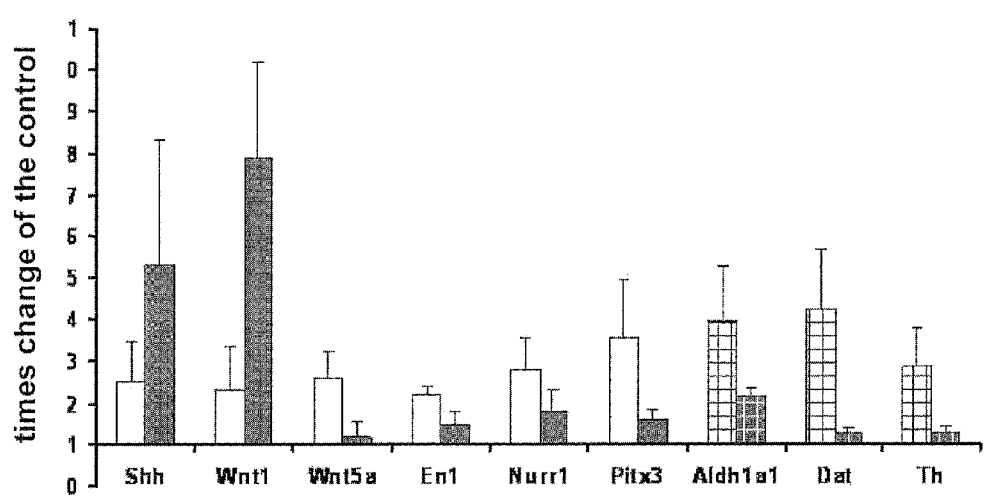
FIG. 7 Evidence of gene expression of neurotrophic transcription factors and dopamine markers with real-time-RT-PCR after incubation with 50 µM 9-methyl-β-carboline for 48 hours 10 DIV-12 DIV.

For this purpose, real-time-RT-PCR experiments were carried out. In this quantitative method the transcription of selected genes is measured. We selected genes which are enhanced under proliferation and differentiation conditions and such that are of importance for the formation, stability and degradation of dopaminergic neurons. The analyses were conducted in midbrain cultures after exposition to 50 µM 9-methyl-β-carboline for 48 hours and 48 hours after removal of 9-methyl-β-carboline. Control cultures were kept simultaneously under the same conditions. The results are shown in FIG. 7. These experiments showed that in the cultures with 9-methyl-β-carboline those factors were activated which stimulate the differentiation of precursor cells to neuronal cells (Sonic Hedgehog) and those which activate the formation of tyrosin hydroxylase-positive neurons (dopaminergic neurons) (Wnt 1, Wnt 5a, engrailed 1, Nurr 1, and Pitx 3). Moreover, factors were increased which are activated during the formation of dopaminergic precursor cells (progenitor cells) (Aldh1a1), the dopamine transporter (DAT) and tyrosin hydroxylase.

These findings were further sustained by so-called microarray methods. The analyses confirm that the transcription of genes involved in neuronal differentiation is increased. Interestingly, genes which activate inflammation processes are transcribed less than in control cultures. Genes involved in apoptosis were transcribed less.

Results

Altogether, the analyses show that 9-Alkyl-β-carboline derivatives induce and stabilize dopaminergic neurons and that 9-Alkyl-β-carboline derivatives have a general cell-protective effect which is also beneficial for other nerve cell types. These effects have a considerable therapeutic potential for the treatment of neurodegenerative diseases, in particular Parkinson's disease, Alzheimer's disease and movement disorders.

Example 7

Evidence for Growth-Accelerating Effects on Cells

The cell growth increasing effect of the compounds according to the general formula (I) can be used in particular for the cultivation of dopaminergic cells and also for stem cells which shall be engrafted for the treatment of Parkinson's disease.

To verify if 9-methyl-β-carboline increases the efficiency of culture media for the experiments with neurons and for tissue engineering, pilot experiments were carried out by way of example with undifferentiated multipotent neuronal precursor cells from the midbrain of mouse embryos (embryonic day 14). By suitable cultivation procedures a cell suspension was produced which was kept for four weeks in a medium that contained, inter alia, growth factors from fibroblasts and the skin (epidermal growth factor). After this time the neuronal precursor cells were differentiated in a medium to promote the maturation of neurons. After a week, about 40% of the cells could be stained by a neuronal marker (β-tubulin, type III). Most other cells were glial cells. A small percentage of the neurons could be colored additionally with the antibody for tyrosin hydroxylase (~3%). This means that about three percent of the neurons were from the dopaminergic cell type. The enzyme tyrosin hydroxylase can only be found in the midbrain in dopaminergic neurons. To further substantiate this result it was shown by the real-time RT-PCR method that, apart of tyrosin hydroxylase, the culture contains other proteins characteristic for dopaminergic neurons, namely the dopamine transporter DAT and the aldehyde dehydrogenase 1A1 (ALDH 1A1).

Under corresponding conditions 9-methyl-β-carboline (50 µM final concentration) were added to the culture medium once per week, also once to the differentiation medium. The amount of neurons significantly increased compared to control conditions (+15%, 3 independent experiments), while the percentage of dopaminergic cells even increased by 25%. These results clearly prove that the compounds according to the general formula (I) by way of example of 9-methyl-β-carboline initiate the neogenesis of neurons and precursor cells develop preferably to dopaminergic neurons. The compounds according to the general formula (I) thus are suitable for studying neuronal differentiation in general and for generating a culture with a relatively high percentage of dopaminergic neurons. This is for example of great interest for the implantation in patients suffering from Parkinson's disease in which above all dopaminergic neurons degenerated. Moreover, the compounds according to the general formula (I) are thus suitable for tissue engineering where certain cell types and in particular neurons (i.e. hippocampal granule cells) shall be proliferated in a directed manner. The use of compounds according to the general formula (I) in cell cultures leads to an acceleration of cell growth which is of great interest in particular in neurons, bone cells, stem cells, endothelial cells and other cells designated for implantation and which significantly improves the treatment of leukemia or neurodegenerative diseases.

Example 8

To investigate Parkinson's disease acute in vivo models are used for years although chronic models would be a better model for the disease. Another disadvantage of the acute models is that ca. 40% of the animals die from the application of the neurotoxin. Therefore, we have chosen a chronic model in which comparably very low doses of neurotoxin 1-methyl-4-phenylpyridinium ($MPP^+$) were infused for 28 days into the left lateral ventricle of the rat brain. The substance was continuously applied through osmotic minipumps. Thereby, casualties were completely avoided. After four weeks, either solvent or equimolar amounts of the sample substance, namely neuroprotective betacarboline, resp. 9-alkyl-betacarboline was infused for two weeks via the same catheter. In a preliminary study for dose-finding the $MPP^+$ dose which leads to a reduction by 40% of the dopamine concentration in the striatum was determined. The dopamine concentration in the striatum is a characteristic marker for Parkinson's disease in which a degeneration of dopaminergic neurons occurs.

Figure 8:
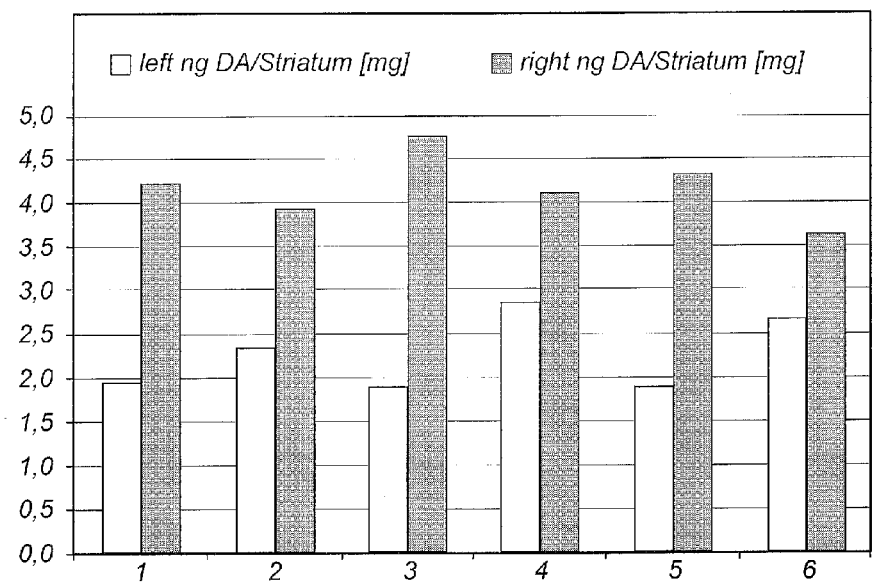
FIG. 8 shows the dopamine level (ng/mg tissue) in the striatum of the rat after infusion for 6 weeks in the rat's left ventricle of the brain in the beginning with MPP+ (0.284 mg/kg/day) for the first 4 weeks and for the last two weeks NaI as vehicle (sodium iodide: 0.0716 mg/kg/day). In the diagram the dopamine (DA) levels of the left and right striatum of the single rats are indicated.
Figure 9:
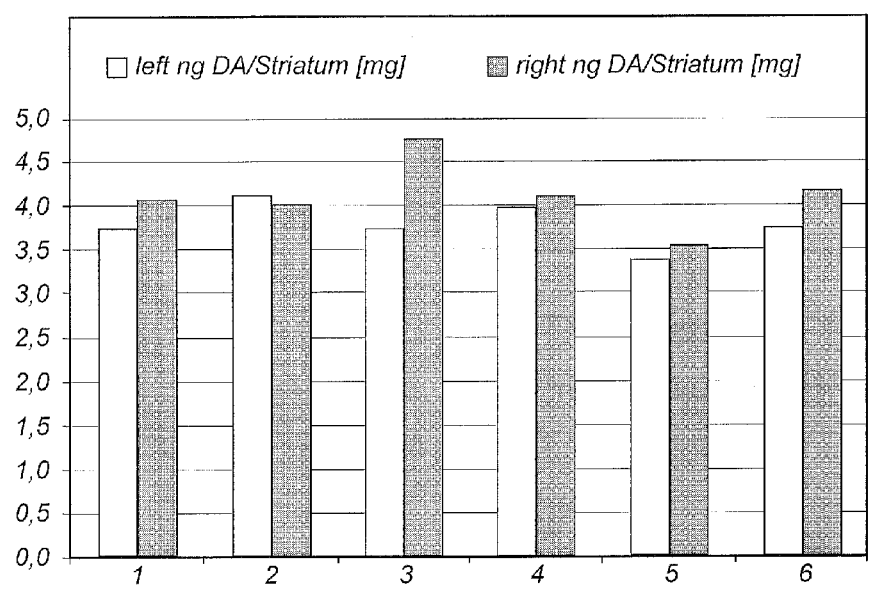
FIG. 9 shows the dopamine level (ng/mg tissue) in the striatum of the rat after infusion for 6 weeks in the rat's left ventricle of the brain in the beginning with MPP+ (0.284 mg/kg/day) for the first 4 weeks and for the last two weeks with 9-methyl-betacarboline (0.105 mg/kg/day).

The results are shown in FIGS. 8 and 9. It resulted that the dopamine concentration only decreased on the left side in which the neurotoxin $MPP^+$ had been infunded while the concentration on the right side corresponded to that of the control rats. In contrast to this, betacarboline, resp. 9-alkyl-betacarboline normalized the concentration on the left side if it has been infunded in equimolar concentrations during the two weeks after $MPP^+$.

An explanation for the effect of the betacarboline was found in the tests of the RNA from the striata of these rats through the PCR superarray method. Accordingly, the betacarboline activates the generation of neurotrophins, thus proteins produced naturally in the body, which are responsible for the growth and differentiation of neurons. For example, brain-derived neurotrophic factor (BDNF) increased by 4.9 times in the left striatum compared to rats which had only been infunded a solvent for six weeks. The finding is remarkable that the increase of BDNF was even higher in the right striatum (8.5 times). It is known that neurodegenerative processes in the brain are followed by compensatory reactions. Moreover, dopaminergic neurons project extensions from the substantia nigra, the brain area in which their cell bodies are located, to the contralateral striatum.

The concentration of another neurotrophin, glial cell line-derived neurotrophic factor (GDNF), did not increase in the left but in the right striatum by factor 12. This finding is very interesting because the infusion of the protein GDNF effected a growth of cellular extensions of dopaminergic neurons in the anterior putamen of patients suffering from Parkinson's disease and an improvement in clinical symptoms (Love et al., Nature Medicine, 2005, 11, 703).

In conclusion, the in vivo tests show that 9-methyl-β-carboline has a neuroprotective effect in an established model of Parkinson's disease. In this model, mainly dopaminergic neurons are damaged. The conclusion therefore only refers to this neuronal type. The basic mechanism is an activation of neurotrophins which are known for playing a decisive role in the neogeneration of neurons in adulthood.

Examples 9-20

Anti-Parkinson Test of the Compounds A to L

The compounds A to L were tested as described in example 8. The test results of the compounds A to L are indicated in the following table in comparison to 9-methyl-β-carboline.

TABLE 1

Compounds A to L in comparison to 9-methyl-β-carboline

| 9-methyl-β-carboline | Standard |
|---|---|
| Compound A | + |
| Compound B | ± |
| Compound C | ± |
| Compound D | + |
| Compound E | + |
| Compound F | ± |
| Compound G | ± |
| Compound H | + |
| Compound I | − |
| Compound J | ± |
| Compound K | ± |
| Compound L | + |

+: slightly better than 9-methyl-β-carboline
±: the same as 9-methyl-β-carboline
−: slightly worse than 9-methyl-β-carboline Example 21

Synthesis of 9-methyl-β-carboline

Synthesis Scheme for 9-methyl-β-carboline

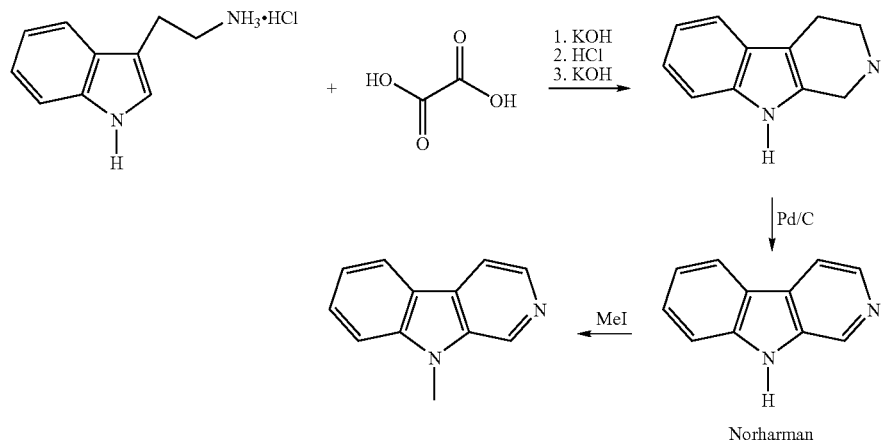

Norharman

A stirred solution of 13 g (0.0756 mol) 1,2,3,4-tetrahydro-β-carboline, produced of tryptamine hydrochloride and glyoxal acid, as described by Ho and Walker (1988), and 2.6 g of Pd/C (10%) in 600 ml cumene were refluxed under nitrogen atmosphere for 90 minutes. After adding 100 ml ethanol the heated solution was filtered and the carbon was extracted with 3×30 ml heated ethanol. The combined liquid fractions were concentrated and the remainder crystallized from toluene for obtaining 10.5 g (82%) of norharman. The methylation in position 9 was carried out as described in literature (Ho B T, McIsaac W M, Walker K E, Estevez V, J Pharm Sci 57: 269, 1968), but with an improved processing: 1 g (5.95 mmol) of norharman was dissolved in 10 ml dry DMF under nitrogen atmosphere. Then 0.36 g (14.9 mmol) sodium hydride was added as a 60% dispersion in petroleum at 0° C. After the mixture cooled down to room temperature it was cooled down to −10° C. and 0.84 g (5.95 mmol) methyl iodide were added. After continued stirring for 12 hours, the mixture was again cooled down to room temperature. All volatile components were removed under reduced pressure. Then 100 ml of water were added and the mixture was extracted with 3×50 ml $CHCl_3$. The combined organic fractions were washed with 5×20 ml water and concentrated for drying. The remainder was transferred into 100 ml of 2N hydrochloric acid. To isolate the educt of the desired methylated product an ion pair extraction of the HCl salt was carried out in $CHCl_3$ and in a liquid/liquid extractor for 2 days. After removing the solvent 0.7 g (64%) of yellow crystals of 9-methyl-β-carboliniumhydrochloride were obtained.

Melting point: 295°; GC/MS for the free base: m/z=182 (100%), 167 (5%), 140 (10%), 127 (10%), 113 (5%), 91 (10%). $^1$H-NMR (HCl salt): δ (ppm) methanol d4, 250 MHz: 4.06 s, 3H, N—$CH_3$; 7.28-7.35, dt, J=1.2; 6.8, 1H, H6; 7.58-7.70, m, 2H, H7, H8; 8.13-8.16, d, J=5.4, 1H, H4; 8.18-8.21, d, J=7.9, 1H H5; 8.31-8.33, d, J=5.4, 1H, H3; 8.89, s, 1H, H1.

Examples 22-33

Production of Compounds A to L

The synthesis of compounds A to L occurs according to example 21 in which the corresponding alkyl iodides, alkyl bromides or alkyl tosylates are used. The yields are between 30 and 75% of the theory.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for the treatment of restless legs syndrome, Alzheimer's disease, Parkinson's disease, Lewy bodies disease, frontotemporal dementia, Lytico-Bodig disease (Parkinsonism-dementia-amyotrophic lateral sclerosis) or striatonigral degeneration comprising administering to a subject who would benefit from such treatment a therapeutically effective amount of a pharmaceutical composition containing a compound of the general formula (I)

$$(I)$$

wherein
$R^1$ stands for one of the following moieties:
—$R^{16}$, —$CR^4R^5R^6$, —X—$CR^4R^5R^6$, —X—$R^4$, —CO—NH—$R^{16}$, —CO—$R^{16}$;
$R^2$ and $R^3$ mean the following moieties independent from one another: —H, —$R^7$, —$R^8$, —$CR^9R^{10}R^{11}$—$CR^{12}R^{13}R^{14}$, —Y—$CR^9R^{10}R^{11}$, —Z—$CR^{12}R^{13}R^{14}$, —Y—$R^{15}$, —Z—$R^{15}$, —O—$R^{17}$, —S—$R^{18}$, —NH—$R^{19}$, —CO—NH—$R^{20}$, —CO—O—$R^{21}$;
X can be selected from —$(CH_2)_n$—, —CH=CH—, —C≡C—, —$CH_2$—CO—, —CO—, —CO—$CH_2$—;
Y, Z mean independent from one another: —$(CH_2)_m$—, —CH=CH—, —C≡C—, —O—$(CH_2)_p$—, —NH—$(CH_2)_q$—, —NH—CO—, —CO—, —O—CO—;
m, p, q each represent an integer between 1 and 4 independent from one another;
n represents an integer between 1 and 6
$R^4$-$R^{15}$ mean the following moieties independent from one another: —H, —OH, —$OCH_3$, —$OC_2H_5$, —$OC_3H_7$, —O-cyclo-$C_3H_5$, —$OCH(CH_3)_2$, —$OC(CH_3)_3$, —$OC_4H_9$, —OPh, —$OCH_2$-Ph, —$OCPh_3$, —SH, —$SCH_3$, —$SC_2H_5$, —$SC_3H_7$, —S-cyclo-$C_3H_5$, —$SCH(CH_3)_2$, —$SC(CH_3)_3$, —$NO_2$, —F, —Cl, —Br, —I, —$N_3$, —CN, —OCN, —NCO, —SCN, —NCS, —CHO, —$COCH_3$, —$COC_2H_5$, —$COC_3H_7$, —CO-cyclo-$C_3H_5$, —$COCH(CH_3)_2$, —$COC(CH_3)_3$, —COOH, —COCN, —$COOCH_3$, —$COOC_2H_5$, —$COOC_3H_7$, —COO-cyclo-$C_3H_5$, —$COOCH(CH_3)_2$, —$COOC(CH_3)_3$, —OOC—$CH_3$, —OOC—$C_2H_5$, —OOC—$C_3H_7$, —OOC-cyclo-$C_3H_5$, —OOC—$CH(CH_3)_2$, —OOC—$C(CH_3)_3$, —$CONH_2$, —$CONHCH_3$, —$CONHC_2H_5$, —$CONHC_3H_7$, —CONH-cyclo-$C_3H_5$, —$CONH[CH(CH_3)_2]$, —$CONH[C(CH_3)_3]$, —$CON(CH_3)_2$, —$CON(C_2H_5)_2$, —$CON(C_3H_7)_2$, —CON(cyclo-$C_3H_5)_2$, —$CON[CH(CH_3)_2]_2$, —$CON[C(CH_3)_3]_2$, —$NHCOCH_3$, —$NHCOC_2H_5$, —$NHCOC_3H_7$, —NHCO-cyclo-$C_3H_5$, —NHCO—$CH(CH_3)_2$, —NHCO—$C(CH_3)_3$, —NHCO—$OCH_3$, —NHCO—$OC_2H_5$, —NHCO—$OC_3H_7$, —NHCO—O-cyclo-$C_3H_5$, —NHCO—$OCH(CH_3)_2$, —NHCO—$OC(CH_3)_3$, —$NH_2$, —$NHCH_3$, —$NHC_2H_5$, —NH—CO—N[CH(CH_3)_2]_2$, —NH—CO—N[C(CH_3)_3]_2$, —NH—CS—$NH_2$, —NH—CS—$NHCH_3$, —NH—CS—$NHC_2H_5$, —NH—CS—$NHC_3H_7$, —NH—CS—NH-cyclo-$C_3H_5$, —NH—CS—NH[CH(CH_3)_2]$, —NH—CS—NH[C(CH_3)_3]$, —NH—CS—N(CH_3)_2$, —NH—CS—N(C_2H_5)_2$, —NH—CS—N(C_3H_7)_2$, —NH—CS—N(cyclo-$C_3H_5)_2$, —NH—CS—N[CH(CH_3)_2]_2$, —NH—CS—N[C(CH_3)_3]_2$, —NH—C(—NH)—$NH_2$, —NH—C(—NH)—$NHCH_3$, —NH—C(—NH)—$NHC_2H_5$ —$CH_2$—$CH(CH_3)_2$, —$CH(CH_3)$—$C_2H_5$, —$C(CH_3)_3$, —$C_5H_{11}$, —$CH(CH_3)$—$C_3H_7$, —$CH_2$—$CH(CH_3)$—$C_2H_5$, —$CH(CH_3)$—$CH(CH_3)_2$, —$C(CH_3)_2$—$C_2H_5$, —$CH_2$—$C(CH_3)_3$, —$CH(C_2H_5)_2$, —$C_2H_4$—$CH(CH_3)_2$, —$C_6H_{13}$, —$C_3H_6$—$CH(CH_3)_2$, —$C_2H_4$—$CH(CH_3)$—$C_2H_5$, —$CH(CH_3)$—$C_4H_9$, —$CH_2$—$CH(CH_3)$—$C_3H_7$, —$CH(CH_3)$—$CH_2$—$CH(CH_3)_2$, —$CH(CH_3)$—$CH(CH_3)$—$C_2H_5$, —$CH_2$—$CH(CH_3)$—$CH(CH_3)_2$, —$CH_2$—$C(CH_3)_2$—$C_2H_5$, —$C(CH_3)_2$—$C_3H_7$, —$C(CH_3)_2$—$CH(CH_3)_2$, —$C_2H_4$—$C(CH_3)_3$, —$CH(CH_3)$—$C(CH_3)_3$, —CH=$CH_2$, —$CH_2$—CH=$CH_2$, —$C(CH_3)$=$CH_2$, —CH=CH—$CH_3$, —$C_2H_4$—CH=$CH_2$, —$C_7H_{15}$, —$C_8H_{17}$, —$CH_2$—CH=CH—$CH_3$, —CH=CH—$C_2H_5$ —$CH_2$—$C(CH_3)$=$CH_2$, —$CH(CH_3)$—CH=CH, —CH=$C(CH_3)_2$, —$C(CH_3)$=CH—$CH_3$, —CH=CH—CH=$CH_2$, —$C_3H_6$—CH=$CH_2$, —$C_2H_4$—CH=CH—$CH_3$, —$CH_2$—CH=CH—$C_2H_5$, —$CH_2$—CH=CH—$C_3H_7$, —$CH_2$—CH=CH—$CH_2$, —CH=CH—CH=CH—$CH_3$, —CH=CH—$CH_2$—CH=$CH_2$, —$C(CH_3)$=CH—$CH_2$, —CH=$C(CH_3)$—CH=$CH_2$, —CH=CH—$C(CH_3)$=$CH_2$, —$C_2H_4$—$C(CH_3)$=$CH_2$, —$CH_2$—$CH(CH_3)$—CH=$CH_2$, —$CH(CH_3)$—$CH_2$—CH=$CH_2$—$CH_2$, —CH=$C(CH_3)$—$CH_2$—$C(CH_3)$=CH—$CH_3$, —$CH(CH_3)$—CH=CH—$CH_3$, —CH=CH—$CH(CH_3)_2$, —CH=$C(CH_3)$—$C_2H_5$, —$C(CH_3)$=CH—$C_2H_5$, —$C(CH_3)$=$C(CH_3)_2$, —$C(CH_3)_2$—CH=$CH_2$, —$CH(CH_3)$—$C(CH_3)$=$CH_2$, —$C(CH_3)$=CH—CH—$CH_2$, —CH=$C(CH_3)$—CH=$CH_2$, —CH=CH—$C(CH_3)$=$CH_2$, —$C_4H_8$—CH=$CH_2$, —$C_3H_6$—CH=CH—$CH_3$, —$C_2H_4$—CH=CH—$C_2H_5$, —$CH_2$—CH=CH—$C_3H_7$, —CH=CH—$C_4H_9$, —$C_3H_6$—$C(CH_3)$=$CH_2$, —$CH_2$—$CH_2$—$CH_2$—$OCH_3$, —$C_2H_4$—$CH(CH_3)$—CH=$CH_2$, —$CH_2$—$CH(CH_3)$—$CH_2$—CH=$CH_2$, —$CH_2NH_2$, —$CH(CH_3)$—$C_2H_4$—CH=$CH_2$, —$C_2H_4$—CH=$C(CH_3)_2$, —$C_2H_4$—$C(CH_3)$=CH—$CH_3$, —$CH_2$—$CH(CH_3)$—CH=CH—$CH_3$, —$CH(CH_3)$—$CH_2$—CH=CH—$CH_3$, —$CH_2OH$, —$CH_2SH$, —$CH_2$—CH=CH—$CH(CH_3)_2$, —$CH_2$—CH=$C(CH_3)$—$C_2H_5$, —$CH_2$—$CH_2$—$CH_2NH_2$, —$CH_2$—$C(CH_3)$=CH—$C_2H_5$, —$CH(CH_3)$—CH=CH—$C_2H_5$, —$CH_2$—$CH_2NH_2$, —CH=CH—$CH_2$—$CH(CH_3)_2$, —CH=CH—$CH(CH_3)$—$C_2H_5$, —CH=$C(CH_3)$—$C_3H_7$, —$C(CH_3)$=CH—$C_3H_7$, —$CH_2$—$CH(CH_3)$—$C(CH_3)$=$CH_2$, —$CH_2$—$CH_2SH$, —$CH(CH_3)$—$CH_2$—$C(CH_3)$=$CH_2$, —$CH(CH_3)$—$CH(CH_3)$—CH=$CH_2$, —$CH_2$—$CH_2$—$CH_2OH$, —$CH_2$—$C(CH_3)_2$—CH=$CH_2$, —$C(CH_3)_2$—$CH_2$—CH=$CH_2$, —$CH_2$—$C(CH_3)$=$C(CH_3)_2$, —$CH(CH_3)$—CH=$C(CH_3)_2$, —$C(CH_3)_2$—CH=CH—

CH₃, —CH₂—CH₂—CH₂SH, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)=CH—CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[C(CH₃)₃]=CH₂, —C[CH(CH₃)(C₂H₅)]=CH₂, —C[CH₂—CH(CH₃)₂]=CH₂, —C₂H₄—CH=CH—CH=CH₂, —C₆H₄—OCH₃, —CH₂—CH=CH—CH₂—CH=CH₂, —CH=CH—C₂H₄—CH=CH₂, —C₆H₄—OH, —CH₂—CH=CH—CH=CH—CH₃, —CH=CH—CH₂—CH=CH—CH₃, —CH₂—CH₂—OCH₃, —CH=CH—CH=CH—C₂H₅, —CH₂—CH=CH—C(CH₃)=CH₂, —CH₂—CH₂OH, —CH₂—CH=C(CH₃)—CH=CH₂, —CH₂—C(CH₃)=CH—CH=CH₂, —CH₂—OCH₃, —CH(CH₃)—CH=CH—CH=CH₂, —CH=CH—CH₂—C(CH₃)=CH₂, —CH=CH—CH(CH₃)—CH=CH₂, —CH=C(CH₃)—CH₂—CH=CH₂, —C(CH₃)=CH—CH₂—CH=CH₂, —CH=CH—CH=C(CH₃)₂, —CH₂—C₆H₄—OCH₃, —CH=CH—C(CH₃)=CH—CH₃, —CH=C(CH₃)—CH=CH—CH₃, —CH₂—C₆H₄—OH, —C(CH₃)=CH—CH=CH—CH₃, —CH=C(CH₃)—C(CH₃)=CH₂, —C(CH₃)=CH—C(CH₃)=CH₂, —C(CH₃)=C(CH₃)—CH=CH₂, —CH=CH—CH=CH—CH=CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —CH₂—CH(CH₃)—C≡CH, —CH(CH₃)—CH₂—C≡CH—CH(CH₃)—C≡C—CH₃, —C₄H₈—C≡CH, —C₃H₆—C≡C—CH₃, —C₂H₄—C≡C—C₂H₅, —CH₂—C≡C—C₃H₇, —C≡C—C₄H₉, —C≡C—C(CH₃)₃, —C₂H₄—CH(CH₃)—C≡CH, —CH₂—CH(CH₃)—CH₂—C≡CH, —CH₂—C≡C—CH(CH₃)₂, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —C≡C—CH(CH₃)—C₂H₅, —C≡C—CH₂—CH(CH₃)₂, —CH(C₂H₅)—C≡C—CH₃, —C(CH₃)₂—C≡C—CH₃, —CH(C₂H₅)—CH₂—C≡CH, —C(CH₃)₂—CH₂—C≡CH, —CH₂—C(CH₃)₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —C≡C—C≡CH, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡CH, —CH₂—C≡C—C≡C—CH₃, —C≡C—CH₂—C≡C—CH₃, —C≡C—C≡C—C₂H₅, —C≡C—CH(CH₃)—C≡CH, —CH(CH₃)—C≡C—C≡CH, —CH(C≡CH)—CH₂—C≡CH, —C(C≡CH)₂—CH₃, —CH₂—CH(C≡CH)₂, —CH(C≡CH)—C≡C—CH₃;

$R^{16}$-$R^{21}$ mean the following moieties independent from one another:

—CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, cyclo-C₃H₅, cyclo-C₄H₇, cyclo-C₅H₉, cyclo-C₆H₁₁, cyclo-C₇H₁₃, cyclo-C₈H₁₅, -Ph, —CH₂-Ph, —CPh₃, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₃H₆—CH(CH₃)₂, —C₂H₄—CH(CH₃)—C₂H₅, —CH(CH₃)—C₄H₉, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH=CH₂, —CH₂—CH=CH₂, —C(CH₃)=CH₂, —CH=CH—CH₃, —C₂H₄—CH=CH₂, —C₇H₁₅, —C₈H₁₇, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—C₂H₅, —CH=CH—C₃H₇, —CH₂—CH=CH—CH=CH₂, —CH=CH—CH₂—CH=CH—CH₃, —CH₂—CH=CH—CH₂—CH=CH₂, —C(CH₃)=CH—CH=CH₂, —CH=C(CH₃)—CH=CH₂, —CH=CH—C(CH₃)=CH₂, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=C—C(CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, —C(CH₃)₂—CH=CH—CH₂, —CH=CH—C(CH₃)=CH₂, —C₄H₈—CH=CH₂, —C₃H₆—CH=CH—CH₃, —C₂H₄—CH=CH—C₂H₅, —CH₂—CH=CH—C₃H₇, —CH=CH—C₄H₉, —C₃H₆—C(CH₃)=CH₂, —CH₂—CH₂—CH₂—OCH₃, —C₂H₄—CH(CH₃)—CH=CH₂, —CH₂—CH(CH₃)—CH₂—CH=CH₂, —CH₂NH₂, —CH(CH₃)—C₂H₄—CH=CH₂, —C₂H₄—CH=C(CH₃)₂, —C₂H₄—C(CH₃)=CH—CH₃, —CH₂—CH(CH₃)—CH=CH—CH₃, —CH(CH₃)—CH₂—CH=CH—CH₃, —CH₂OH, —CH₂SH, —CH₂—CH=CH—CH(CH₃)₂, —CH₂—CH=C(CH₃)—C₂H₅, —CH₂—CH₂—CH₂NH₂, —CH₂—C(CH₃)=CH—C₂H₅, —CH(CH₃)—CH=CH—C₂H₅, —CH₂—CH₂NH₂, —CH=CH—CH₂—CH(CH₃)₂, —CH=CH—CH(CH₃)—C₂H₅, —CH=C(CH₃)—C₃H₇, —C(CH₃)=CH—C₃H₇, —CH₂—CH(CH₃)—C(CH₃)=CH₂, —CH₂—CH₂SH, —CH(CH₃)—CH₂—C(CH₃)=CH₂, —CH(CH₃)—CH=CH₂, —CH₂—CH₂—CH₂OH, —CH₂—C(CH₃)₂—CH=CH₂, —C(CH₃)₂—CH₂—CH=CH₂, —CH₂—C(CH₃)=C(CH₃)₂, —CH(CH₃)—CH=C(CH₃)₂, —C(CH₃)₂—CH=CH—CH₃, —CH₂—CH₂—CH₂SH, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)=CH—CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[C(CH₃)₃]=CH₂, —C[CH(CH₃)(C₂H₅)]=CH₂, —C[CH₂—CH(CH₃)₂]=CH₂, —C₂H₄—CH=CH—CH=CH₂, —C₆H₄—OCH₃, —CH₂—CH=CH—CH₂—CH=CH₂, —CH=CH—C₂H₄—CH=CH₂, —C₆H₄—OH, —CH₂—CH=CH—CH=CH—CH₃, —CH=CH—CH₂—CH=CH—CH₃, —CH₂—CH₂—OCH₃, —CH=CH—CH=CH—C₂H₅, —CH₂—CH=CH—

—C(CH₃)=CH₂, —CH₂—CH₂OH, —CH₂—CH=C(CH₃)—CH=CH₂, —CH₂—C(CH₃)=CH—CH=CH₂, —CH₂—OCH₃, —CH(CH₃)—CH=CH—CH=CH₂, —CH=CH—CH₂—C(CH₃)=CH₂, —CH=CH—CH(CH₃)—CH=CH₂, —CH=C(CH₃)—CH₂—CH=CH₂, —C(CH₃)=CH—CH₂—CH=CH₂, —CH=CH—CH=C(CH₃)₂, —CH₂—C₆H₄—OCH₃, —CH=CH—C(CH₃)=CH—CH₃, —CH=C(CH₃)—CH=CH—CH₃, —CH₂—C₆H₄—OH, —C(CH₃)=CH—CH=CH—CH₃, —CH=C(CH₃)—C(CH₃)=CH₂, —C(CH₃)=CH—C(CH₃)=CH₂, —C(CH₃)=C(CH₃)—CH=CH₂, —CH=CH—CH=CH—CH=CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —CH₂—CH(CH₃)—C≡CH, —CH(CH₃)—CH₂—C≡CH, —CH(CH₃)—C≡C—CH₃, —C₄H₈—C≡CH, —C₃H₆—C≡C—CH₃, —C₂H₄—C≡C—C₂H₅, —CH₂—C≡C—C₃H₇, —C≡C—C₄H₉, —C≡C—C(CH₃)₃, —C₂H₄—CH(CH₃)—C≡CH, —CH₂—CH(CH₃)—CH₂—C≡CH, —CH₂—C≡C—CH(CH₃)₂, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —C≡C—CH(CH₃)—C₂H₅, —C≡C—CH₂—CH(CH₃)₂, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —C≡C—C≡CH, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡CH, —CH₂—C≡C—C≡C—CH₃, —C≡C—CH₂—C≡C—CH₃, —C≡C—C₂H₅, —C≡C—CH(CH₃)—C≡CH, —CH(CH₃)—C≡C—C≡CH, —CH(C≡CH)—CH₂—C≡CH, —C(C≡CH)₂—CH₃, —CH₂—CH(C≡CH)₂, —CH(C≡CH)—C≡C—CH₃;

or a pharmaceutically acceptable salt, solvate, hydrate, complex compound, enantiomer, diastereomer or racemate of the aforementioned compound.

2. The method according to claim 1 wherein the pharmaceutical composition contains a compound of the general formula (V)

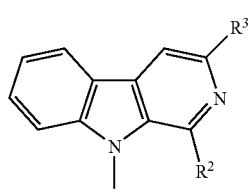

(V)

wherein the moieties R² and R³ have the meaning described in claim 1.

3. The method according to claim 1, wherein the compound is selected from the group consisting of 9-methyl-9H-β-carboline, 9-propyl-9H-β-carboline, 9-[(1Z)-1-methylprop-1-enyl]-9H-β-carboline, 1-chloro-9-[(1Z,3E)-2-methylpenta-1,3-dienyl]-9H-β-carboline, 1-chloro-9-methyl-9H-β-carboline, 1,3-dichloro-9-methyl-9H-β-carboline, 3-iodo-9-methyl-9H-β-carboline, 1-bromo-9-methyl-9H-β-carboline, 1-methoxy-3-chloro-9-methyl-9H-β-carboline, 1,9-dimethyl-9H-β-carboline, 1-isopropyl-3.9-dimethyl-9H-β-carboline, 3.9-dimethyl-9H-β-carboline, 3-ethyl-9-methyl-9H-β-carboline, 3-methyl-9H-β-carboline, and 3-isopropyl-9H-β-carboline.

* * * * *